(12) United States Patent
Marvanyos et al.

(10) Patent No.: US 10,023,566 B2
(45) Date of Patent: Jul. 17, 2018

(54) DASATINIB SALTS

(71) Applicant: EGIS GYOGYSZERGYAR ZRT, Budapest (HU)

(72) Inventors: Ede Laszlo Marvanyos, Budapest (HU); Attila Virag, Budapest (HU); Tamas Gregor, Csomor (HU); Balazs Volk, Budapest (HU); Maria Tothne Lauritz, Budapest (HU); Laszlo Pongo, Kerepes (HU); Balazs Peregi, Pomaz (HU); Gyula Lukacs, Budapest (HU); Zoltan Varga, Budapest (HU); Andras Dancso, Budapest (HU)

(73) Assignee: EGIS GYOGYSZERGYAR ZRT, Budapest (HU)

( * ) Notice: Subject to any disclaimer, the term of this patent is extended or adjusted under 35 U.S.C. 154(b) by 0 days.

(21) Appl. No.: 15/314,255

(22) PCT Filed: May 26, 2015

(86) PCT No.: PCT/HU2015/000049
§ 371 (c)(1),
(2) Date: Nov. 28, 2016

(87) PCT Pub. No.: WO2015/181573
PCT Pub. Date: Dec. 3, 2015

(65) Prior Publication Data
US 2017/0183334 A1    Jun. 29, 2017

(30) Foreign Application Priority Data
May 26, 2014   (HU) ..................................... 1400264

(51) Int. Cl.
*C07D 417/12*   (2006.01)
(52) U.S. Cl.
CPC ........ *C07D 417/12* (2013.01); *C07B 2200/13* (2013.01)
(58) Field of Classification Search
CPC .................................................. C07D 417/12
See application file for complete search history.

(56) References Cited

U.S. PATENT DOCUMENTS

| 2007/0105867 A1 | 5/2007 | Chidambaram et al. |
| 2008/0275009 A1 | 11/2008 | Chidambaram et al. |

FOREIGN PATENT DOCUMENTS

| WO | 2005077945 A2 | 8/2005 |
| WO | 2007035874 A1 * | 3/2007 |
| WO | 2007035874 A1 * | 3/2007 |

OTHER PUBLICATIONS

Bighley—Swarbrick, Ency. Pharm. Technology Ch. 13, (Marcel Dekker, NY1996) pp. 453-499.*
International Search Report for PCT/HU2015/000049 dated Jul. 31, 2015.
Lombardo, L. J. et al., "Discovery of N-(2-chloro-6-methylphenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays," Journal of Medicinal Chemistry, Dec. 7, 2004, vol. 47, No. 27, pp. 6658-6661.

* cited by examiner

*Primary Examiner* — Alexander R Pagand
*Assistant Examiner* — Ebenezer Sackey
(74) *Attorney, Agent, or Firm* — Millen White Zelano and Branigan, PC; Csaba Henter

(57) ABSTRACT

The invention relates to normal or acidic salts of dasatinib and the hydrate and solvate forms thereof. More specifically the invention concerns: dasatinib cyclamic acid salt, dasatinib cyclamic acid (1:1) salt Form I, dasatinib cyclamic acid (1:1) salt Form II, dasatinib hydrogen bromide (1:2) salt, dasatinib methane sulfonic acid (1:2) salt, dasatinib p-toluenesulfonic acid (1:1) dihydrate salt, anhydrous dasatinib p-toluenesulfonic acid (1:1) salt Form I, anhydrous dasatinib p-toluenesulfonic acid (1:1) salt Form II, dasatinib p-toluenesulfonic acid (1:1) salt methanol solvate. Moreover the invention relates process for preparing dasatinib salts, pharmaceutical compositions comprising thereof and the use of dasatinib salts the treatment of cancer.

21 Claims, 8 Drawing Sheets

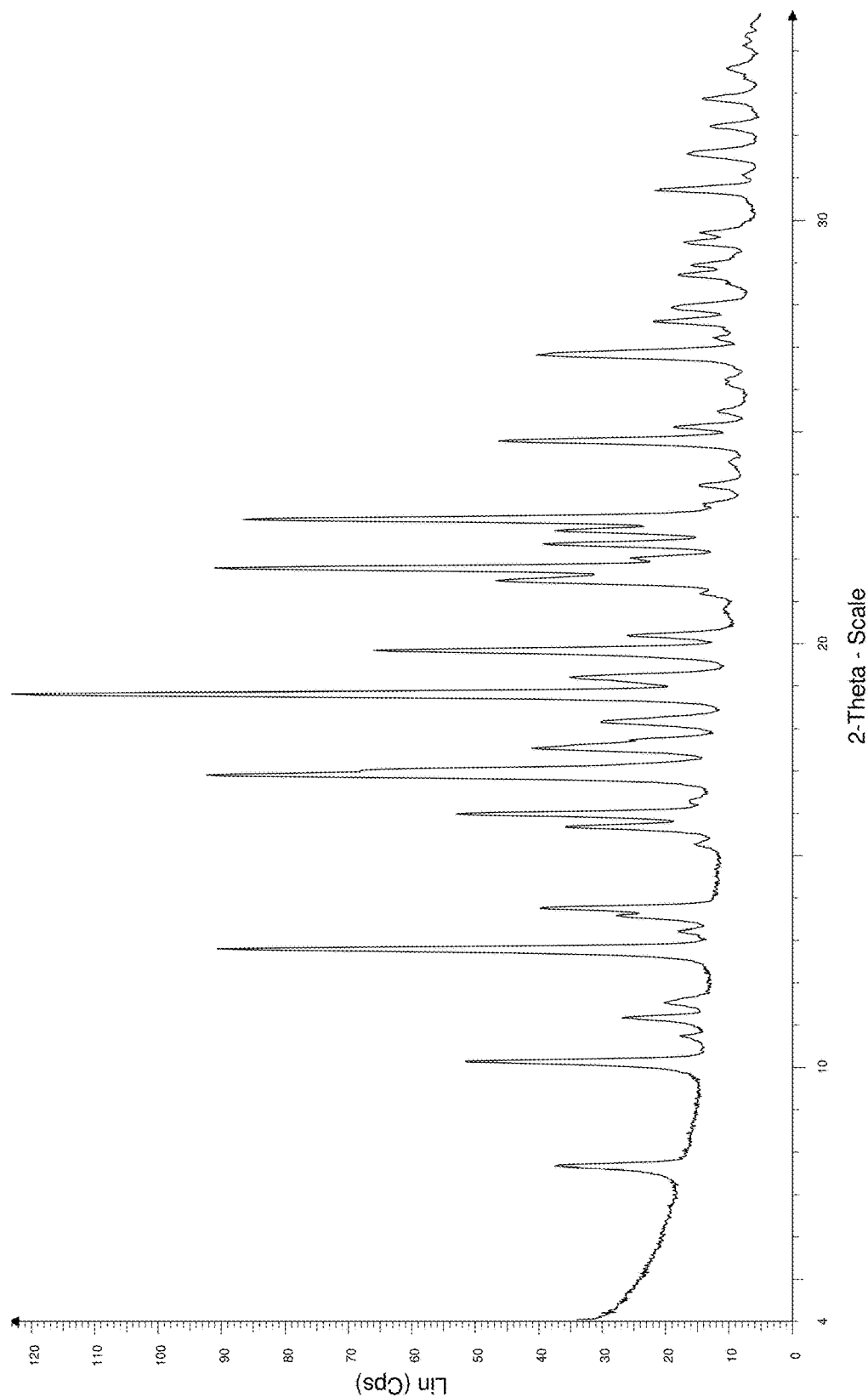
Figure 1: The X-ray powder diffraction pattern of dasatinib cyclamate (1:1) Form I

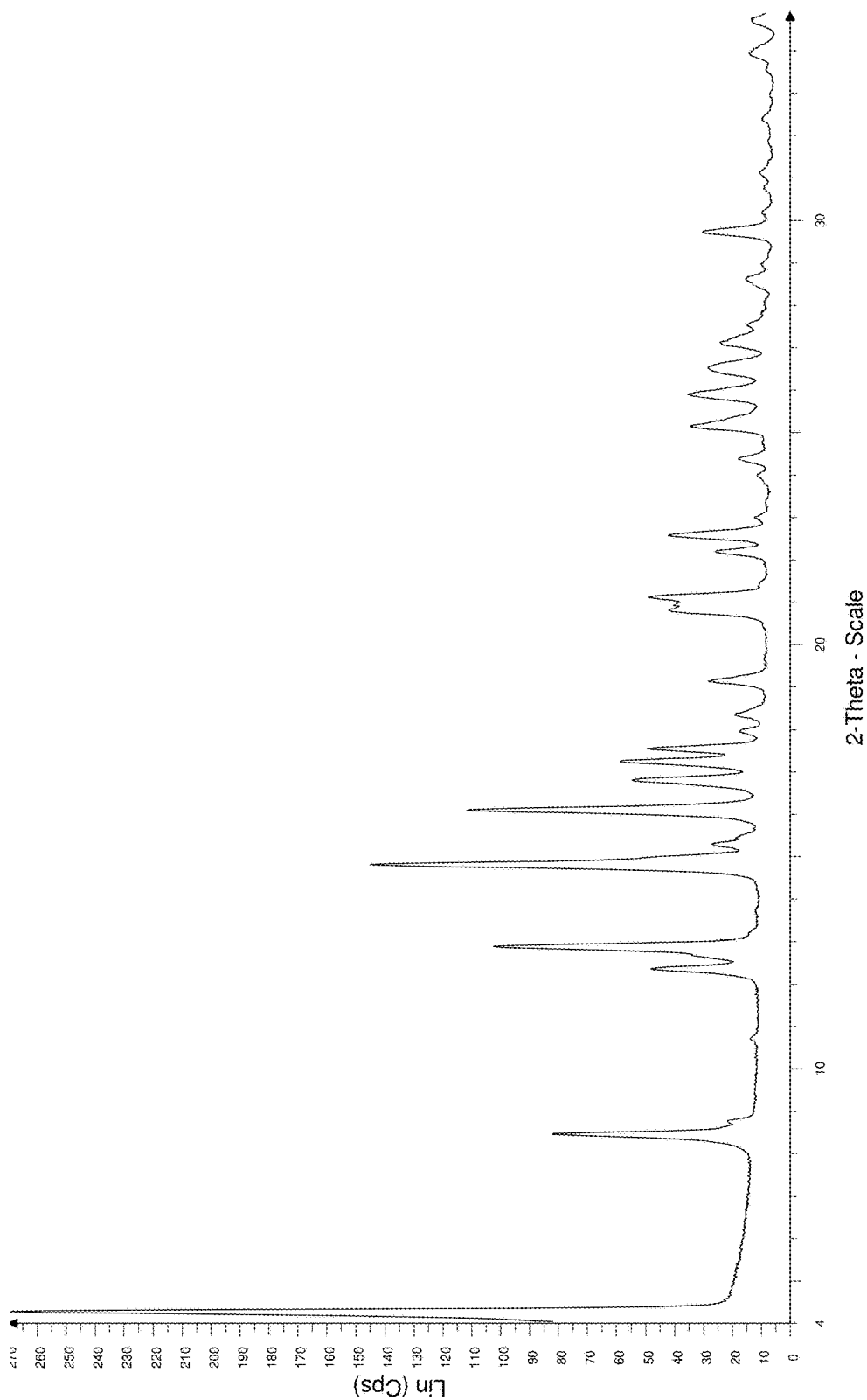
Figure 2: The X-ray powder diffraction pattern of dasatinib cyclamate (1:1) Form II

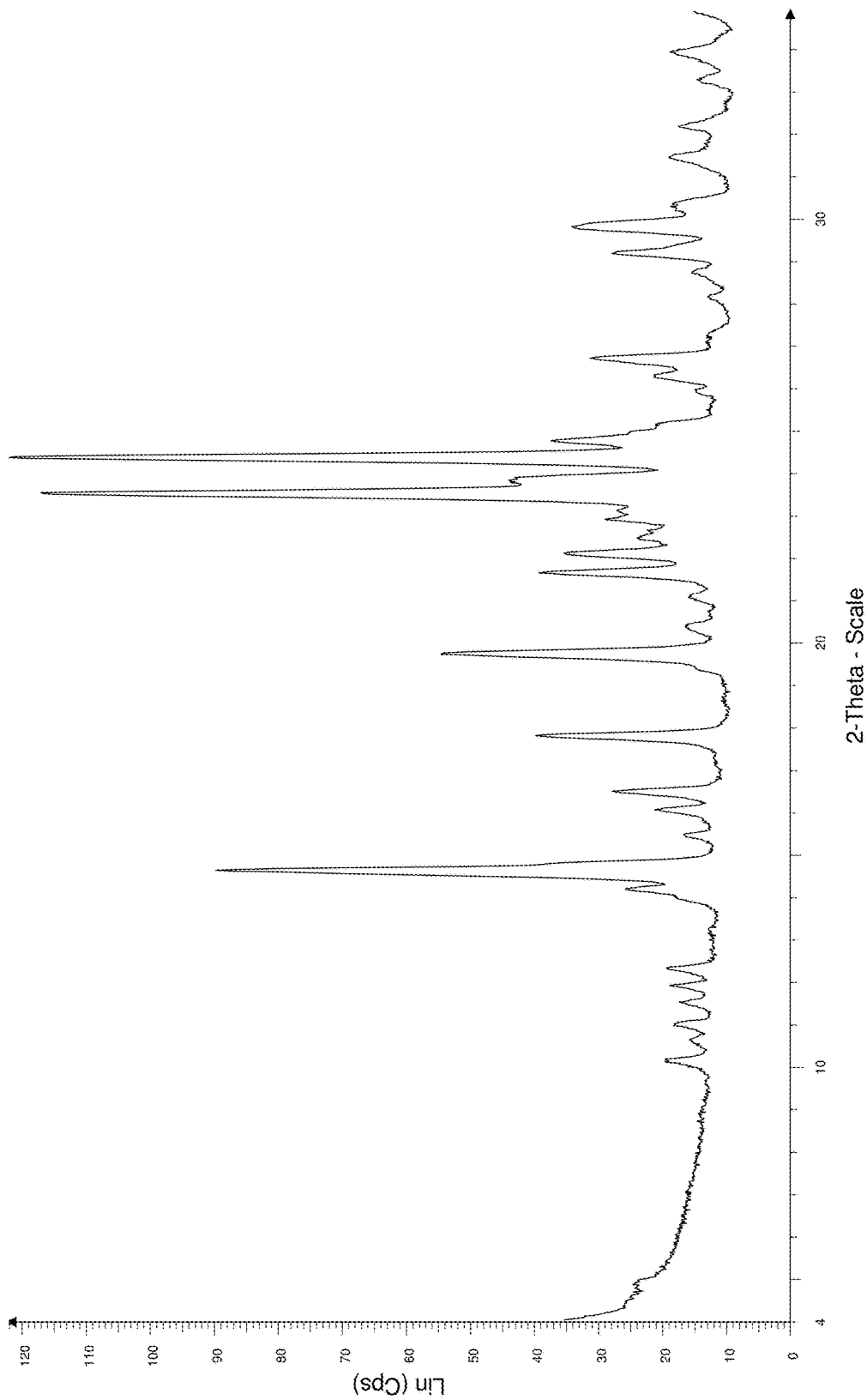
Figure 3: The X-ray powder diffraction pattern of dasatinib hydrogen bromide (1:2) salt

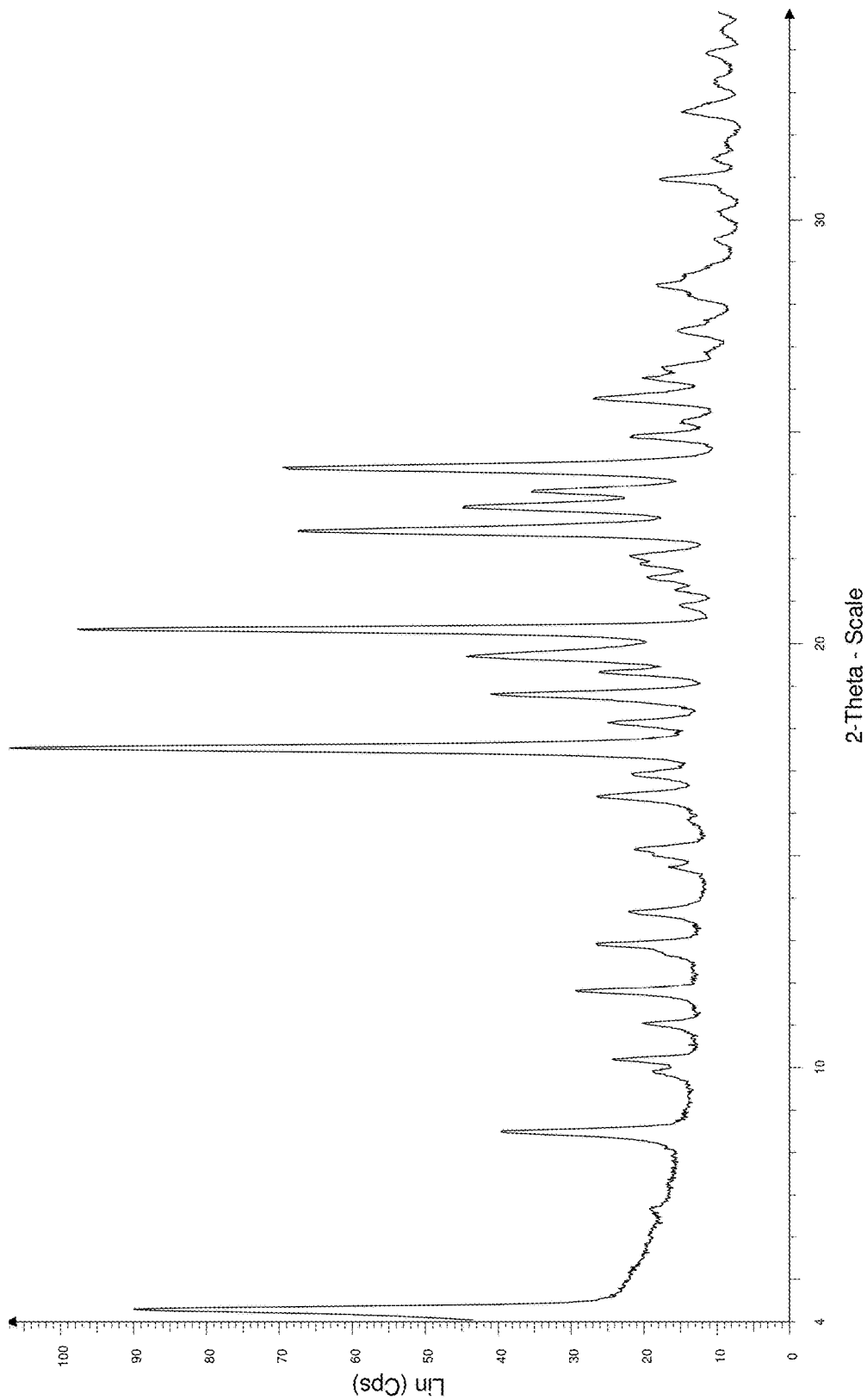

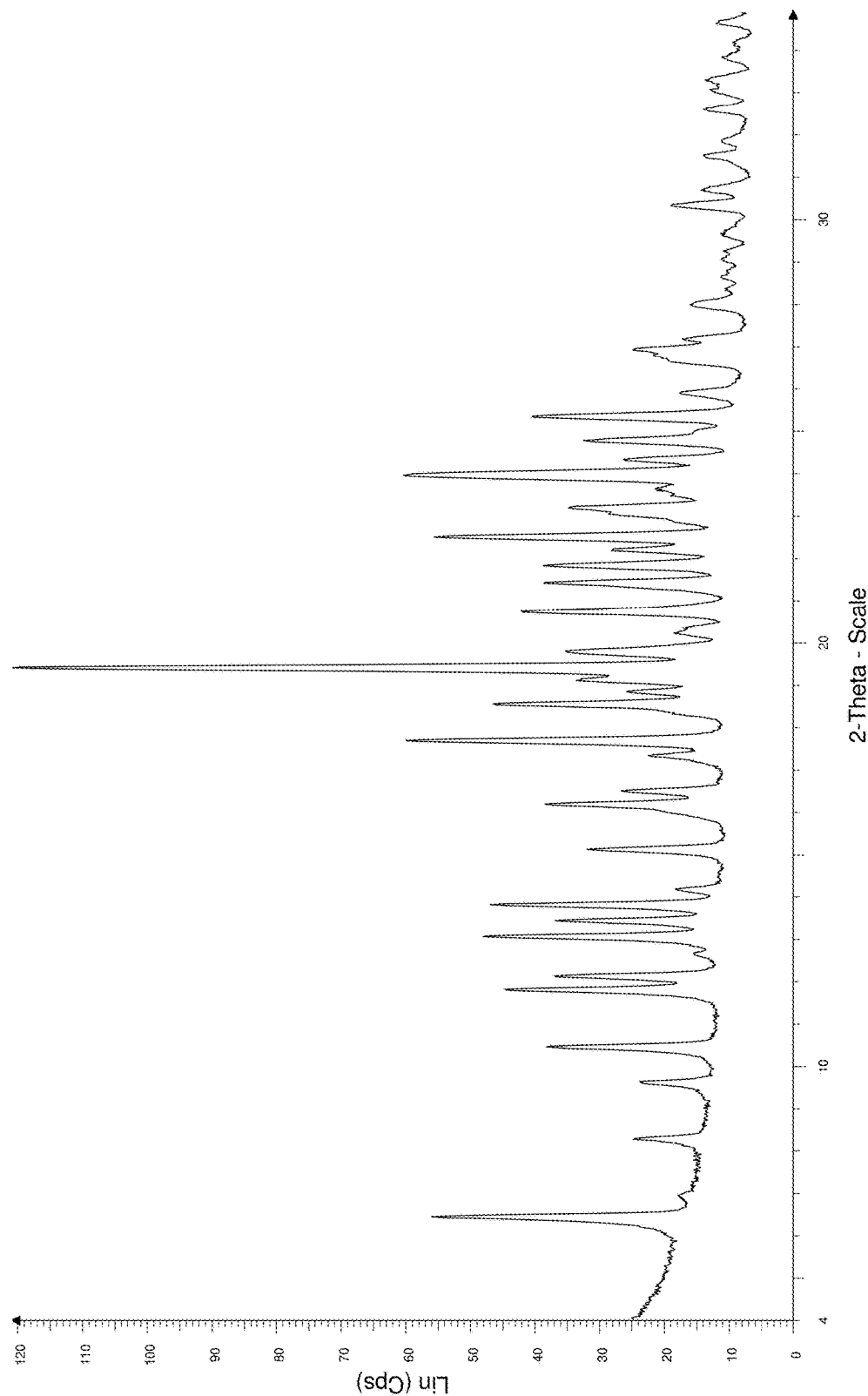
Figure 5: The X-ray powder diffraction pattern of dasatinib tosilate (1:1) dihydrate

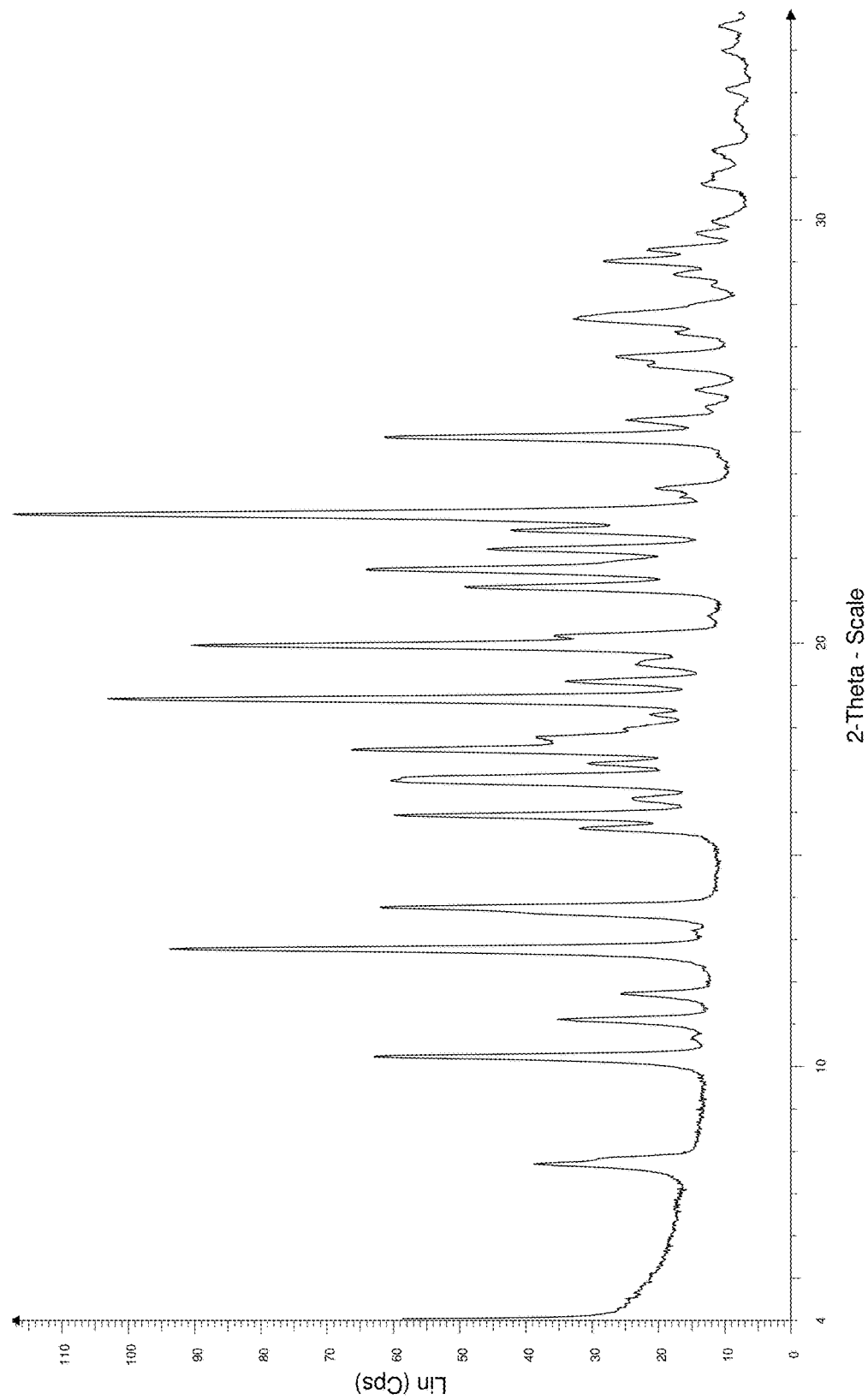
Figure 6: The X-ray powder diffraction pattern of anhydrous dasatinib tosilate (1:1) Form I

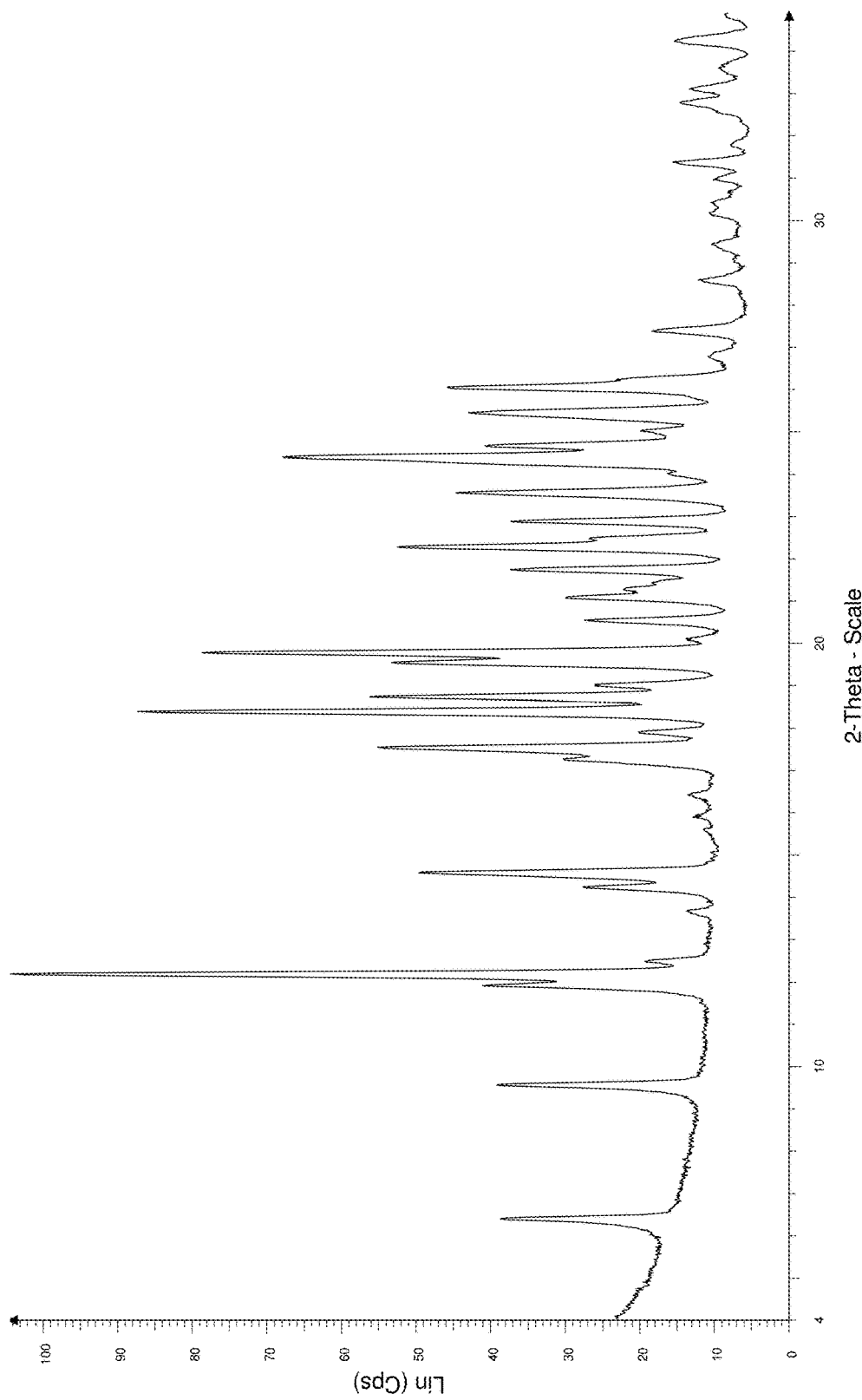

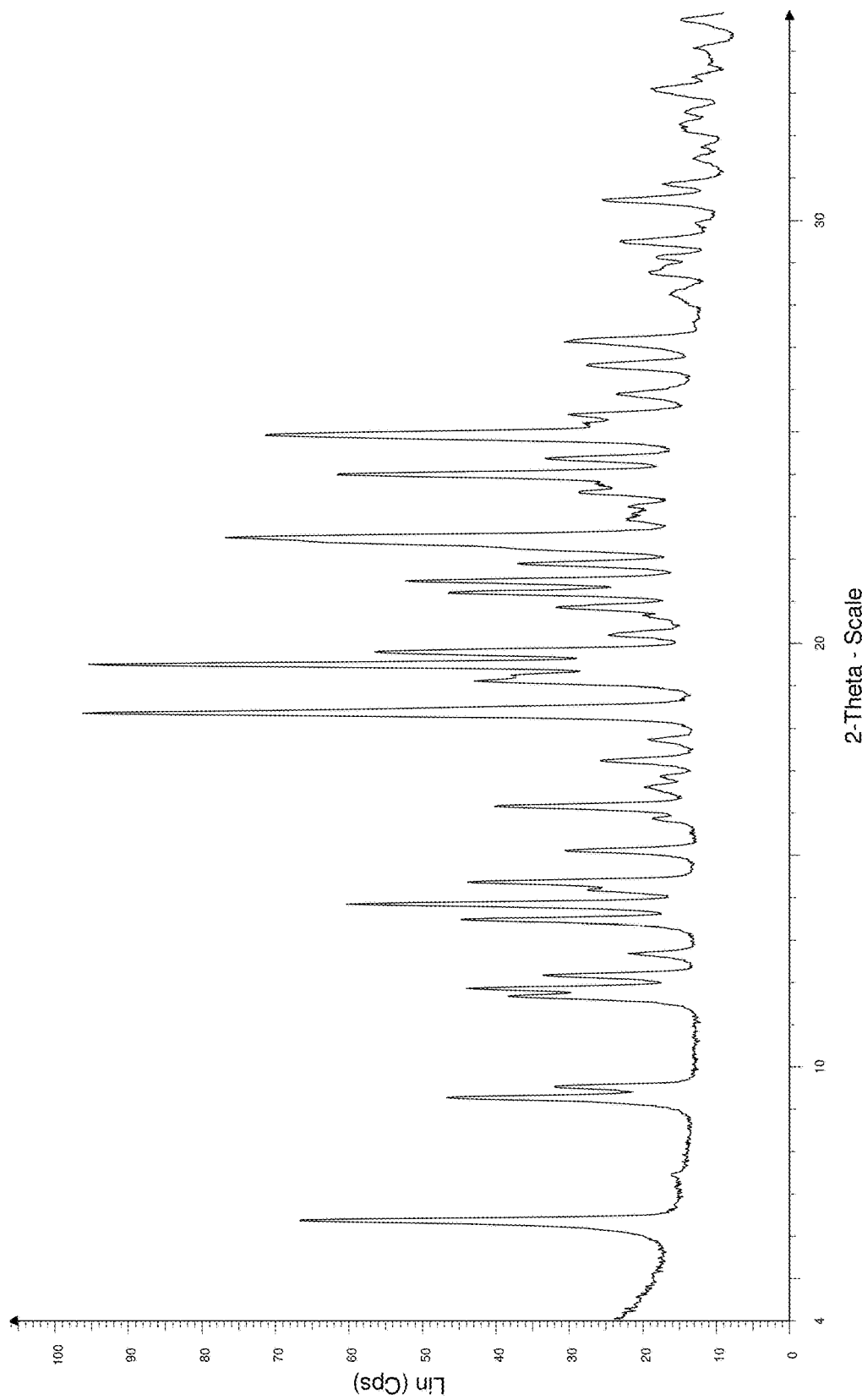
Figure 8: The X-ray powder diffraction pattern of dasatinib tosilate (1:1) methanol solvate

DASATINIB SALTS

TECHNICAL FIELD

The invention is in the field of pharmaceuticals, more specifically in the field of protein kinase inhibitors. Even more specifically the invention relates to new salts of N-(2-Chloro-6-methylphenyl)-2-[6-[4-(2-hydroxyethyl)piperazin-1-yl]-2-methylpyrimidin-4-ylamino]-1,3-thiazole-5-carboxamide, anhydrous forms, hydrates and solvates thereof, process for the preparation thereof, pharmaceutical compositions containing the same and use of said salts in therapy.

The structure of N-(2-Chloro-6-methylphenyl)-2-[6-[4-(2-hydroxyethyl)piperazin-1-yl]-2-methylpyrimidin-4-ylamino]-1,3-thiazole-5-carboxamide (INN: dasatinib) of the formula (1) is:

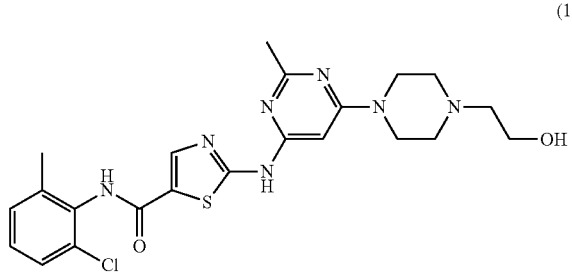

(1)

BACKGROUND ART

It is known in the art, that dasatinib is a protein kinase inhibitor, which acts due to the inhibition of Bcr-Abl tyrosine-kinase enzyme. This enzyme is produced by the leukemic cells and it allows the cells to proliferate without being regulated by cytokines. The proliferation of leukemic cells can be blocked by inhibition of Bcr-Abl kinase or other kinases. Dasatinib is indicated in the therapy of the following forms of leukemia:

a) newly diagnosed Philadelphia chromosome positive (Ph+) chronic myelogenous leukemia (CML) in the chronic phase.
b) chronic, accelerated or blast phase CML with resistance or intolerance to prior therapy including imatinib mesilate.
c) Ph+ acute lymphoblastic leukemia (ALL) and lymphoid blast CML with resistance or intolerance to prior therapy.

Dasatinib of the formula 1 is firstly disclosed in WO 2000/062778 A1.

Dasatinib HCl salt and antitumor activity thereof is disclosed by Lombardo et al (Lombardo, L. J. et al., *J. Med. Chem.* 2004, 47, 6658-6661).

Crystalline n-butanol solvate (BU-2) and crystalline monohydrate (H1-7) of dasatinib are disclosed in WO2005/077945. Example 8 of the application describes the preparation of dasatinib monohydrate started from the aqueous solution of the acetate salt of dasatinib.

Further dasatinib salts are disclosed in WO 2007/035874. Several organic and inorganic acid addition salt of dasatinib is exemplified. The salts obtained by using mainly the high-throughput crystallization screening technique mostly contain solvent adsorbed on the surface or in the form of solvate. These salts in this form are unsuitable for pharmaceutical product development.

THE OBJECT OF THE INVENTION

There is a serious demand in pharmaceutical industry on the reproducible manufacture of morphologically uniform and suitably pure products. This is a fundamental demand for active ingredients required to meet the requirements of pharmaceutical formulation, quality assurance and those authorities responsible for marketing authorization. It is well-known in the state of the art that various salts and polymorphs differ from each other in important properties such as solubility, chemical stability, polymorph stability, dissolution rate, bioavailability, amenability to filtration or drying and in tabletting properties. Furthermore, it is very important from economical point of view that the process is suitable for an industrial scale application, can be reproduced easily and results in a morphologically uniform product with suitable purity.

Dasatinib base monohydrate is poorly soluble in aqueous medium thus its bioavailability is restricted. The poor solubility also limits the route of administration and the preparation of the active ingredient into solid pharmaceutical composition. The common inventive concept of the present invention resides in the preparation of new salts of dasatinib of formula (1) which are more soluble in aqueous medium than the dasatinib (monohydrate) base.

The object of the present invention is to provide morphologically uniform new dasatinib salts of high purity which possess more favourable physical-chemical properties than the known salts and have at least as high chemical stability as dasatinib monohydrate or the known salts and can be prepared in a reproducible manner suitable for industrial scale manufacture.

BRIEF DESCRIPTION OF THE DRAWINGS

FIG. 1: The X-ray powder diffraction pattern of dasatinib cyclamate (1:1) Form I
FIG. 2: The X-ray powder diffraction pattern of dasatinib cyclamate (1:1) Form II
FIG. 3: The X-ray powder diffraction pattern of dasatinib hydrogen bromide (1:2) salt
FIG. 4: The X-ray powder diffraction pattern of dasatinib mesilate (1:2)
FIG. 5: The X-ray powder diffraction pattern of dasatinib tosilate (1:1) dihydrate
FIG. 6: The X-ray powder diffraction pattern of anhydrous dasatinib tosilate (1:1) Form I
FIG. 7: The X-ray powder diffraction pattern of anhydrous dasatinib tosilate (1:1) Form II
FIG. 8: The X-ray powder diffraction pattern of dasatinib tosilate (1:1) methanol solvate
The y axis represents the counts per second (Cps) on linear scale [Lin(Cps)] in the coordinate system.

SHORT DESCRIPTION OF THE INVENTION

It has been surprisingly found that the above object is solved according to the present invention by the preparation of the new salts of dasatinib and new polymorphic forms thereof, namely by salts formed with cyclamic acid, hydrogen bromide, methane sulfonic acid, and p-toluenesulfonic acid.

N-cyclohexyl sulfamic (cyclamic) acid addition salts of dasatinib have never been disclosed in the prior art, yet.

The invention relates to normal or acidic salts of dasatinib and the hydrate and solvate forms thereof. More specifically the invention concerns:

dasatinib cyclamic acid salt,
dasatinib cyclamic acid (1:1) salt Form I,
dasatinib cyclamic acid (1:1) salt Form II,
dasatinib hydrogen bromide (1:2) salt,
dasatinib methane sulfonic acid (1:2) salt,
dasatinib p-toluenesulfonic acid (1:1) dihydrate salt,
anhydrous dasatinib p-toluenesulfonic acid (1:1) salt Form I,
anhydrous dasatinib p-toluenesulfonic acid (1:1) salt Form II,
dasatinib p-toluenesulfonic acid (1:1) salt methanol solvate.

DETAILED DESCRIPTION OF THE INVENTION

More specifically the invention relates to crystalline dasatinib cyclamic acid (1:1) salt Form I, which has the following characteristic X-ray powder diffraction peaks: 2θ (±0.2 °2θ): 10.11; 18.81; 19.83. More particularly this product can be characterized by the following characteristic X-ray powder diffraction peaks: 2θ (±0.2 °2θ): 7.64; 10.11; 13.74; 18.81; 19.83; 21.49; 21.78; 22.94; 24.79; 31.59. The most specifically, this product can be characterized by the following characteristic X-ray powder diffraction peaks: 2θ (±0.2 °2θ): 7.64; 10.11; 10.72; 11.15; 11.50; 12.78; 13.19; 13.56; 13.74; 15.25; 15.66; 15.97; 16.29; 16.89; 17.53; 18.15; 18.81; 19.20; 19.83; 20.18; 21.18; 21.49; 21.78; 22.02; 22.35; 22.68; 22.94; 23.30; 23.74; 24.31; 24.79; 25.12; 25.50; 26.83; 27.23; 27.63; 27.96; 28.73; 28.95; 29.50; 29.73; 30.72; 31.59; 32.23; 32.89; 33.60. The characteristic X-ray powder diffractogram of the product is shown on FIG. 1. The signals having intensity larger than 1% are summarized in Table 1 below.

TABLE 1 dasatinib cyclamic acid (1:1) salt Form I
(relative intensity >1%)

| Peak | 2θ (°) | d (Å) | Relative intensity |
|---|---|---|---|
| 1 | 7.64 | 11.56 | 18 |
| 2 | 10.11 | 8.74 | 33 |
| 3 | 10.72 | 8.25 | 4 |
| 4 | 11.15 | 7.93 | 12 |
| 5 | 11.50 | 7.69 | 6 |
| 6 | 12.78 | 6.92 | 69 |
| 7 | 13.19 | 6.71 | 5 |
| 8 | 13.56 | 6.53 | 14 |
| 9 | 13.74 | 6.44 | 25 |
| 10 | 15.25 | 5.81 | 4 |
| 11 | 15.66 | 5.65 | 22 |
| 12 | 15.97 | 5.55 | 37 |
| 13 | 16.29 | 5.44 | 5 |
| 14 | 16.89 | 5.25 | 72 |
| 15 | 17.53 | 5.06 | 27 |
| 16 | 18.15 | 4.88 | 18 |
| 17 | 18.81 | 4.71 | 100 |
| 18 | 19.20 | 4.62 | 22 |
| 19 | 19.83 | 4.47 | 50 |
| 20 | 20.18 | 4.40 | 15 |
| 21 | 21.18 | 4.19 | 5 |
| 22 | 21.49 | 4.13 | 33 |
| 23 | 21.78 | 4.08 | 73 |
| 24 | 22.02 | 4.03 | 15 |
| 25 | 22.35 | 3.97 | 27 |
| 26 | 22.68 | 3.92 | 26 |
| 27 | 22.94 | 3.87 | 69 |
| 28 | 23.30 | 3.82 | 5 |
| 29 | 23.74 | 3.74 | 6 |
| 30 | 24.31 | 3.66 | 2 |
| 31 | 24.79 | 3.59 | 34 |
| 32 | 25.12 | 3.54 | 10 |
| 33 | 25.50 | 3.49 | 4 |
| 34 | 26.83 | 3.32 | 30 |
| 35 | 27.23 | 3.27 | 5 |
| 36 | 27.63 | 3.23 | 14 |
| 37 | 27.96 | 3.19 | 11 |
| 38 | 28.73 | 3.10 | 10 |
| 39 | 28.95 | 3.08 | 9 |
| 40 | 29.50 | 3.03 | 10 |
| 41 | 29.73 | 3.00 | 8 |
| 42 | 30.72 | 2.91 | 14 |
| 43 | 31.59 | 2.83 | 10 |
| 44 | 32.23 | 2.78 | 7 |
| 45 | 32.89 | 2.72 | 8 |
| 46 | 33.60 | 2.66 | 5 |

The present invention is also concerned with the crystalline dasatinib cyclamic acid (1:1) salt Form II, which has the following characteristic X-ray powder diffraction peaks: 2θ (±0.2 °2θ): 4.24; 8.43; 14.80. More particularly this product can be characterized by the following characteristic X-ray powder diffraction peaks: 2θ (±0.2 °2θ): 4.24; 8.43; 8.73; 12.34; 14.80; 17.25; 20.81; 21.12; 25.91; 26.54. The most specifically. this product can be characterized by the following characteristic X-ray powder diffraction peaks: 2θ (±0.2 °2θ): 4.24; 8.43; 8.73; 10.70; 12.34; 12.87; 14.80; 15.29; 16.09; 16.80; 17.25; 17.54; 17.97; 18.36; 19.13; 20.81; 21.12; 22.20; 22.59; 23.02; 24.00; 24.41; 25.16; 25.91; 26.54; 27.15; 27.56; 28.64; 29.76; 31.13; 32.39; 33.96; 34.74. The characteristic X-ray powder diffractogram of the product is shown on FIG. 2. The signals having intensity equal to or larger than 1% are summarized in Table 2 below.

TABLE 2 dasatinib cyclamic acid (1:1) salt Form II
(relative intensity ≥1%)

| Peak | 2θ (°) | d (Å) | Relative intensity |
|---|---|---|---|
| 1 | 4.24 | 20.82 | 100 |
| 2 | 8.43 | 10.48 | 32 |
| 3 | 8.73 | 10.12 | 4 |
| 4 | 10.70 | 8.26 | 1 |
| 5 | 12.34 | 7.16 | 17 |
| 6 | 12.87 | 6.87 | 42 |
| 7 | 14.80 | 5.98 | 62 |
| 8 | 15.29 | 5.79 | 8 |
| 9 | 16.09 | 5.50 | 47 |
| 10 | 16.80 | 5.27 | 21 |
| 11 | 17.25 | 5.14 | 23 |
| 12 | 17.54 | 5.05 | 19 |
| 13 | 17.97 | 4.93 | 4 |
| 14 | 18.36 | 4.83 | 5 |
| 15 | 19.13 | 4.64 | 9 |
| 16 | 20.81 | 4.27 | 16 |
| 17 | 21.12 | 4.20 | 19 |
| 18 | 22.20 | 4.00 | 8 |
| 19 | 22.59 | 3.93 | 16 |
| 20 | 23.02 | 3.86 | 2 |
| 21 | 24.00 | 3.70 | 2 |
| 22 | 24.41 | 3.64 | 5 |
| 23 | 25.16 | 3.54 | 13 |
| 24 | 25.91 | 3.44 | 13 |
| 25 | 26.54 | 3.36 | 10 |

TABLE 2-continued dasatinib cyclamic acid (1:1) salt Form II
(relative intensity ≥1%)

| Peak | 2θ (°) | d (Å) | Relative intensity |
|---|---|---|---|
| 26 | 27.15 | 3.28 | 8 |
| 27 | 27.56 | 3.23 | 4 |
| 28 | 28.64 | 3.11 | 4 |
| 29 | 29.76 | 3.00 | 11 |
| 30 | 31.13 | 2.87 | 2 |
| 31 | 32.39 | 2.76 | 2 |
| 32 | 33.96 | 2.64 | 4 |
| 33 | 34.74 | 2.58 | 3 |

The present invention is also concerned with the crystalline dasatinib hydrogen bromide (1:2) salt, which has the following characteristic X-ray powder diffraction peaks: 2θ (±0.2 °2θ): 19.75; 24.39; 29.82. More particularly this product can be characterized by the following characteristic X-ray powder diffraction peaks: 2θ (±0.2 °2θ): 10.98; 11.51; 12.32; 16.07; 19.75; 21.67; 24.39; 24.78; 29.82; 32.20. The most specifically. this product can be characterized by the following characteristic X-ray powder diffraction peaks: 2θ (±0.2 °2θ): 10.11; 10.63; 10.98; 11.51; 11.91; 12.32; 14.19; 14.63; 15.46; 16.07; 16.50; 17.81; 19.75; 20.39; 21.07; 21.67; 22.14; 22.49; 23.55; 23.86; 24.39; 24.78; 26.30; 26.73; 28.76; 29.22; 29.82; 30.31; 31.51; 32.20; 33.34; 33.99. The characteristic X-ray powder diffractogram of the product is shown on FIG. 3. The signals having an intensity larger than 2% are summarized in Table 3 below.

TABLE 3 dasatinib hydrogen bromide (1:2) salt
(relative intensity >2%)

| Peak | 2θ (°) | d (Å) | Relative intensity |
|---|---|---|---|
| 1 | 10.11 | 8.74 | 6 |
| 2 | 10.63 | 8.31 | 3 |
| 3 | 10.98 | 8.05 | 5 |
| 4 | 11.51 | 7.68 | 5 |
| 5 | 11.91 | 7.42 | 6 |
| 6 | 12.32 | 7.18 | 7 |
| 7 | 14.19 | 6.24 | 13 |
| 8 | 14.63 | 6.05 | 70 |
| 9 | 15.46 | 5.73 | 5 |
| 10 | 16.07 | 5.51 | 10 |
| 11 | 16.50 | 5.37 | 16 |
| 12 | 17.81 | 4.98 | 27 |
| 13 | 19.75 | 4.49 | 40 |
| 14 | 20.39 | 4.35 | 6 |
| 15 | 21.07 | 4.21 | 6 |
| 16 | 21.67 | 4.10 | 26 |
| 17 | 22.14 | 4.01 | 23 |
| 18 | 22.49 | 3.95 | 13 |
| 19 | 23.55 | 3.78 | 95 |
| 20 | 23.86 | 3.73 | 31 |
| 21 | 24.39 | 3.65 | 100 |
| 22 | 24.78 | 3.59 | 25 |
| 23 | 26.30 | 3.39 | 11 |
| 24 | 26.73 | 3.33 | 20 |
| 25 | 28.76 | 3.10 | 6 |
| 26 | 29.22 | 3.05 | 17 |
| 27 | 29.82 | 2.99 | 22 |
| 28 | 30.31 | 2.95 | 9 |
| 29 | 31.51 | 2.84 | 9 |
| 30 | 32.20 | 2.78 | 8 |
| 31 | 33.34 | 2.69 | 5 |
| 32 | 33.99 | 2.64 | 9 |

The present invention is also concerned with the crystalline dasatinib methane sulfonic acid (1:2) salt, which has the following characteristic X-ray powder diffraction peaks: 2θ (±0.2 °2θ): 4.26; 17.52; 22.66. More particularly this product can be characterized by the following characteristic X-ray powder diffraction peaks: 2θ (±0.2 °2θ): 4.26; 9.86; 10.16; 13.66; 17.52; 18.13; 20.33; 22.66; 28.45; 30.97. The most specifically. this product can be characterized by the following characteristic X-ray powder diffraction peaks: 2θ (±0.2 °2θ): 4.26; 8.46; 9.86; 10.16; 11.00; 11.78; 12.89; 13.66; 14.70; 15.13; 16.37; 16.90; 17.52; 18.13; 18.80; 19.33; 19.70; 20.33; 20.90; 21.27; 21.56; 22.07; 22.66; 23.22; 23.59; 24.15; 24.88; 25.22; 25.80; 26.28; 26.53; 27.39; 28.45; 29.57; 30.21; 30.97; 31.46; 32.57; 33.25; 33.96. The characteristic X-ray powder diffractogram of the product is shown on FIG. 4. The signals having intensity larger than 2% are summarized in Table 4 below.

TABLE 4 dasatinib methane sulfonic acid (1:2) salt
(relative intensity >2%)

| Peak | 2θ (°) | d (Å) | Relative intensity |
|---|---|---|---|
| 1 | 4.26 | 20.75 | 58 |
| 2 | 8.46 | 10.44 | 26 |
| 3 | 9.86 | 8.96 | 6 |
| 4 | 10.16 | 8.70 | 12 |
| 5 | 11.00 | 8.03 | 8 |
| 6 | 11.78 | 7.51 | 18 |
| 7 | 12.89 | 6.86 | 15 |
| 8 | 13.66 | 6.48 | 11 |
| 9 | 14.70 | 6.02 | 5 |
| 10 | 15.13 | 5.85 | 10 |
| 11 | 16.37 | 5.41 | 16 |
| 12 | 16.90 | 5.24 | 11 |
| 13 | 17.52 | 5.06 | 100 |
| 14 | 18.13 | 4.89 | 15 |
| 15 | 18.80 | 4.72 | 32 |
| 16 | 19.33 | 4.59 | 17 |
| 17 | 19.70 | 4.50 | 36 |
| 18 | 20.33 | 4.36 | 91 |
| 19 | 20.90 | 4.25 | 6 |
| 20 | 21.27 | 4.17 | 6 |
| 21 | 21.56 | 4.12 | 11 |
| 22 | 22.07 | 4.02 | 13 |
| 23 | 22.66 | 3.92 | 60 |
| 24 | 23.22 | 3.83 | 37 |
| 25 | 23.59 | 3.77 | 27 |
| 26 | 24.15 | 3.68 | 63 |
| 27 | 24.88 | 3.58 | 14 |
| 28 | 25.22 | 3.53 | 7 |
| 29 | 25.80 | 3.45 | 19 |
| 30 | 26.28 | 3.39 | 12 |
| 31 | 26.53 | 3.36 | 10 |
| 32 | 27.39 | 3.25 | 8 |
| 33 | 28.45 | 3.13 | 11 |
| 34 | 29.57 | 3.02 | 3 |
| 35 | 30.21 | 2.96 | 3 |
| 36 | 30.97 | 2.88 | 11 |
| 37 | 31.46 | 2.84 | 4 |
| 38 | 32.57 | 2.75 | 8 |
| 39 | 33.25 | 2.69 | 4 |
| 40 | 33.96 | 2.64 | 5 |

The present invention is also concerned with the crystalline dasatinib p-toluenesulfonic acid (1:1) dihydrate salt, which has the following characteristic X-ray powder diffraction peaks: 2θ (±0.2 °2θ): 6.41; 17.68; 19.41. More particularly this product can be characterized by the following characteristic X-ray powder diffraction peaks: 2θ (±0.2 °2θ): 6.41; 11.79; 13.05; 13.80; 17.68; 18.55; 19.41; 20.73; 22.51; 23.96. The most specifically. this product can be characterized by the following characteristic X-ray powder diffraction peaks: 2θ (±0.2 °2θ): 6.41; 8.25; 9.60; 10.44; 11.79; 12.11; 12.65; 13.05; 13.42; 13.80; 14.17; 15.11; 16.18; 16.50; 17.33; 17.68; 18.55; 18.84; 19.11; 19.41;

19.79; 20.22; 20.73; 21.43; 21.84; 22.20; 22.51; 23.20; 23.96; 24.33; 24.78; 25.36; 25.92; 26.95; 27.19; 28.01; 29.67; 30.36; 30.71; 31.49; 31.85; 32.64; 33.33; 33.87; 34.67. The characteristic X-ray powder diffractogram of the product is shown on FIG. 5. The signals having intensity larger than 3% are summarized in Table 5 below.

TABLE 5 dasatinib p-toluenesulfonic acid (1:1) dihydrate salt
(relative intensity >3%)

| Peak | 2θ (°) | d (Å) | Relative intensity |
|---|---|---|---|
| 1 | 6.41 | 13.78 | 35 |
| 2 | 8.25 | 10.71 | 10 |
| 3 | 9.60 | 9.20 | 10 |
| 4 | 10.44 | 8.46 | 23 |
| 5 | 11.79 | 7.50 | 30 |
| 6 | 12.11 | 7.31 | 23 |
| 7 | 12.65 | 6.99 | 4 |
| 8 | 13.05 | 6.78 | 33 |
| 9 | 13.42 | 6.59 | 23 |
| 10 | 13.80 | 6.41 | 32 |
| 11 | 14.17 | 6.25 | 6 |
| 12 | 15.11 | 5.86 | 19 |
| 13 | 16.18 | 5.47 | 25 |
| 14 | 16.50 | 5.37 | 14 |
| 15 | 17.33 | 5.11 | 11 |
| 16 | 17.68 | 5.01 | 45 |
| 17 | 18.55 | 4.78 | 33 |
| 18 | 18.84 | 4.71 | 14 |
| 19 | 19.11 | 4.64 | 21 |
| 20 | 19.41 | 4.57 | 100 |
| 21 | 19.79 | 4.48 | 23 |
| 22 | 20.22 | 4.39 | 8 |
| 23 | 20.73 | 4.28 | 29 |
| 24 | 21.43 | 4.14 | 26 |
| 25 | 21.84 | 4.07 | 27 |
| 26 | 22.20 | 4.00 | 17 |
| 27 | 22.51 | 3.95 | 42 |
| 28 | 23.20 | 3.83 | 23 |
| 29 | 23.96 | 3.71 | 47 |
| 30 | 24.33 | 3.66 | 16 |
| 31 | 24.78 | 3.59 | 22 |
| 32 | 25.36 | 3.51 | 29 |
| 33 | 25.92 | 3.43 | 9 |
| 34 | 26.95 | 3.31 | 15 |
| 35 | 27.19 | 3.28 | 8 |
| 36 | 28.01 | 3.18 | 8 |
| 37 | 29.67 | 3.01 | 4 |
| 38 | 30.36 | 2.94 | 11 |
| 39 | 30.71 | 2.91 | 6 |
| 40 | 31.49 | 2.84 | 6 |
| 41 | 31.85 | 2.81 | 4 |
| 42 | 32.64 | 2.74 | 6 |
| 43 | 33.33 | 2.69 | 6 |
| 44 | 33.87 | 2.64 | 4 |
| 45 | 34.67 | 2.59 | 4 |

The present invention is also concerned with the anhydrous dasatinib p-toluenesulfonic acid (1:1) salt Form I, which has the following characteristic X-ray powder diffraction peaks: 2θ (±0.2 °2θ): 10.21; 12.77; 16.74. More particularly this product can be characterized by the following characteristic X-ray powder diffraction peaks: 2θ (±0.2 °2θ): 10.21; 11.09; 12.77; 13.75; 16.74; 17.76; 18.68; 19.95; 21.32; 29.04. The most specifically. this product can be characterized by the following characteristic X-ray powder diffraction peaks: 2θ (±0.2 °2θ): 7.68; 10.21; 11.09; 11.70; 12.77; 13.75; 15.62; 15.92; 16.33; 16.74; 17.15; 17.47; 17.76; 18.31; 18.68; 19.10; 19.49; 19.95; 20.18; 21.32; 21.74; 22.22; 22.67; 23.05; 23.66; 24.88; 25.30; 26.01; 26.57; 26.78; 27.33; 27.72; 28.73; 29.04; 29.31; 29.69; 29.99; 30.88; 31.70; 33.13; 34.03; 34.60. The characteristic X-ray powder diffractogram of the product is shown on FIG. 6. The signals having intensity larger than 2% are summarized in Table 6 below.

TABLE 6 anhydrous dasatinib p-toluenesulfonic acid
(1:1) salt Form I (relative intensity >2%)

| Peak | 2θ (°) | d (Å) | Relative intensity |
|---|---|---|---|
| 1 | 7.68 | 11.51 | 22 |
| 2 | 10.21 | 8.65 | 46 |
| 3 | 11.09 | 7.97 | 21 |
| 4 | 11.70 | 7.56 | 13 |
| 5 | 12.77 | 6.93 | 76 |
| 6 | 13.75 | 6.44 | 47 |
| 7 | 15.62 | 5.67 | 20 |
| 8 | 15.92 | 5.56 | 45 |
| 9 | 16.33 | 5.43 | 13 |
| 10 | 16.74 | 5.29 | 46 |
| 11 | 17.15 | 5.17 | 19 |
| 12 | 17.47 | 5.07 | 52 |
| 13 | 17.76 | 4.99 | 26 |
| 14 | 18.31 | 4.84 | 11 |
| 15 | 18.68 | 4.75 | 86 |
| 16 | 19.10 | 4.64 | 22 |
| 17 | 19.49 | 4.55 | 13 |
| 18 | 19.95 | 4.45 | 74 |
| 19 | 20.18 | 4.40 | 24 |
| 20 | 21.32 | 4.16 | 37 |
| 21 | 21.74 | 4.08 | 51 |
| 22 | 22.22 | 4.00 | 34 |
| 23 | 22.67 | 3.92 | 31 |
| 24 | 23.05 | 3.86 | 100 |
| 25 | 23.66 | 3.76 | 11 |
| 26 | 24.88 | 3.58 | 49 |
| 27 | 25.30 | 3.52 | 16 |
| 28 | 26.01 | 3.42 | 6 |
| 29 | 26.57 | 3.35 | 13 |
| 30 | 26.78 | 3.33 | 17 |
| 31 | 27.33 | 3.26 | 9 |
| 32 | 27.72 | 3.22 | 23 |
| 33 | 28.73 | 3.11 | 10 |
| 34 | 29.04 | 3.07 | 20 |
| 35 | 29.31 | 3.04 | 13 |
| 36 | 29.69 | 3.01 | 7 |
| 37 | 29.99 | 2.98 | 5 |
| 38 | 30.88 | 2.89 | 6 |
| 39 | 31.70 | 2.82 | 5 |
| 40 | 33.13 | 2.70 | 3 |
| 41 | 34.03 | 2.63 | 4 |
| 42 | 34.60 | 2.59 | 4 |

The present invention is also concerned with the anhydrous dasatinib p-toluenesulfonic acid (1:1) salt Form II, which has the following characteristic X-ray powder diffraction peaks: 2θ (±0.2 °2θ): 12.17; 14.57; 24.42. More particularly this product can be characterized by the following characteristic X-ray powder diffraction peaks: 2θ (±0.2 °2θ): 6.37; 9.54; 11.90; 12.17; 14.22; 14.57; 18.39; 19.78; 24.42; 25.46. The most specifically. this product can be characterized by the following characteristic X-ray powder diffraction peaks: 2θ (±0.2 °2θ): 6.37; 9.54; 11.90; 12.17; 12.47; 13.66; 14.22; 14.57; 16.42; 17.25; 17.54; 17.90; 18.39; 18.74; 19.01; 19.54; 19.78; 20.08; 20.54; 21.08; 21.74; 22.28; 22.89; 23.58; 24.42; 24.67; 25.04; 25.46; 26.06; 26.79; 27.40; 28.62; 29.46; 30.19; 31.01; 31.39; 32.82; 33.14; 33.65; 34.28. The characteristic X-ray powder diffractogram of the product is shown on FIG. 7. The signals having intensity larger than 3% are summarized in Table 7 below.

TABLE 7 anhydrous dasatinib p-toluenesulfonic acid
(1:1) salt Form II (relative intensity >3%)

| Peak | 2θ (°) | d (Å) | Relative intensity |
|---|---|---|---|
| 1 | 6.37 | 13.86 | 25 |
| 2 | 9.54 | 9.26 | 29 |
| 3 | 11.90 | 7.43 | 32 |
| 4 | 12.17 | 7.27 | 100 |
| 5 | 12.47 | 7.09 | 10 |
| 6 | 13.66 | 6.48 | 4 |
| 7 | 14.22 | 6.22 | 19 |
| 8 | 14.57 | 6.07 | 43 |
| 9 | 16.42 | 5.39 | 5 |
| 10 | 17.25 | 5.14 | 23 |
| 11 | 17.54 | 5.05 | 49 |
| 12 | 17.90 | 4.95 | 12 |
| 13 | 18.39 | 4.82 | 84 |
| 14 | 18.74 | 4.73 | 51 |
| 15 | 19.01 | 4.67 | 19 |
| 16 | 19.54 | 4.54 | 48 |
| 17 | 19.78 | 4.48 | 75 |
| 18 | 20.08 | 4.42 | 6 |
| 19 | 20.54 | 4.32 | 21 |
| 20 | 21.08 | 4.21 | 24 |
| 21 | 21.74 | 4.08 | 32 |
| 22 | 22.28 | 3.99 | 48 |
| 23 | 22.89 | 3.88 | 32 |
| 24 | 23.58 | 3.77 | 40 |
| 25 | 24.42 | 3.64 | 65 |
| 26 | 24.67 | 3.61 | 36 |
| 27 | 25.04 | 3.55 | 14 |
| 28 | 25.46 | 3.50 | 39 |
| 29 | 26.06 | 3.42 | 42 |
| 30 | 26.79 | 3.33 | 5 |
| 31 | 27.40 | 3.25 | 13 |
| 32 | 28.62 | 3.12 | 7 |
| 33 | 29.46 | 3.03 | 5 |
| 34 | 30.19 | 2.96 | 5 |
| 35 | 31.01 | 2.88 | 5 |
| 36 | 31.39 | 2.85 | 11 |
| 37 | 32.82 | 2.73 | 10 |
| 38 | 33.14 | 2.70 | 8 |
| 39 | 33.65 | 2.66 | 4 |
| 40 | 34.28 | 2.61 | 10 |

The present invention is also concerned with the dasatinib p-toluenesulfonic acid (1:1) salt methanol solvate, which has the following characteristic X-ray powder diffraction peaks: 2θ (±0.2 °2θ): 18.36; 19.50; 22.52. More particularly this product can be characterized by the following characteristic X-ray powder diffraction peaks: 2θ (±0.2 °2θ): 6.35; 9.25; 13.83; 18.36; 19.50; 21.48; 22.52; 24.02; 24.94; 27.16. The most specifically. this product can be characterized by the following characteristic X-ray powder diffraction peaks: 2θ (±0.2 °2θ): 6.35; 9.25; 9.51; 11.66; 11.84; 12.15; 12.66; 13.46; 13.83; 14.16; 14.35; 15.09; 15.85; 16.15; 16.61; 17.23; 17.72; 18.36; 19.11; 19.50; 19.80; 20.20; 20.86; 21.20; 21.48; 21.89; 22.52; 23.59; 24.02; 24.39; 24.94; 25.42; 25.91; 26.59; 27.16; 28.80; 29.51; 30.50; 30.88; 32.31; 33.14; 34.77. The characteristic X-ray powder diffractogram of the product is shown on FIG. 8. The signals having intensity larger than 6% are summarized in Table 8 below.

TABLE 8 dasatinib p-toluenesulfonic acid (1:1) salt
methanol solvate (relative intensity >6%)

| Peak | 2θ (°) | d (Å) | Relative intensity |
|---|---|---|---|
| 1 | 6.35 | 13.91 | 60 |
| 2 | 9.25 | 9.55 | 39 |

TABLE 8-continued dasatinib p-toluenesulfonic acid (1:1) salt
methanol solvate (relative intensity >6%)

| Peak | 2θ (°) | d (Å) | Relative intensity |
|---|---|---|---|
| 3 | 9.51 | 9.29 | 22 |
| 4 | 11.66 | 7.59 | 30 |
| 5 | 11.84 | 7.47 | 37 |
| 6 | 12.15 | 7.28 | 25 |
| 7 | 12.66 | 6.99 | 11 |
| 8 | 13.46 | 6.57 | 38 |
| 9 | 13.83 | 6.40 | 57 |
| 10 | 14.16 | 6.25 | 18 |
| 11 | 14.35 | 6.17 | 37 |
| 12 | 15.09 | 5.86 | 22 |
| 13 | 15.85 | 5.59 | 8 |
| 14 | 16.15 | 5.48 | 34 |
| 15 | 16.61 | 5.33 | 10 |
| 16 | 17.23 | 5.14 | 17 |
| 17 | 17.72 | 5.00 | 10 |
| 18 | 18.36 | 4.83 | 100 |
| 19 | 19.11 | 4.64 | 38 |
| 20 | 19.50 | 4.55 | 99 |
| 21 | 19.80 | 4.48 | 54 |
| 22 | 20.20 | 4.39 | 16 |
| 23 | 20.86 | 4.25 | 25 |
| 24 | 21.20 | 4.19 | 42 |
| 25 | 21.48 | 4.13 | 49 |
| 26 | 21.89 | 4.06 | 31 |
| 27 | 22.52 | 3.95 | 78 |
| 28 | 23.59 | 3.77 | 22 |
| 29 | 24.02 | 3.70 | 61 |
| 30 | 24.39 | 3.65 | 27 |
| 31 | 24.94 | 3.57 | 72 |
| 32 | 25.42 | 3.50 | 24 |
| 33 | 25.91 | 3.44 | 16 |
| 34 | 26.59 | 3.35 | 21 |
| 35 | 27.16 | 3.28 | 25 |
| 36 | 28.80 | 3.10 | 12 |
| 37 | 29.51 | 3.02 | 17 |
| 38 | 30.50 | 2.93 | 20 |
| 39 | 30.88 | 2.89 | 10 |
| 40 | 32.31 | 2.77 | 8 |
| 41 | 33.14 | 2.70 | 13 |
| 42 | 34.77 | 2.58 | 7 |

According to a further aspect of the present invention there is provided a process for the preparation of dasatinib salts which comprises reacting the anhydrous crystalline form of dasatinib (1) or hydrate or solvate thereof in a suitable organic solvent with the desired organic or inorganic acid and separating the dasatinib salt formed.

The salts according to the present invention can be prepared by reacting dasatinib free base (1) in an organic solvent with the desired acid at suitable temperature, separating the crystallized salt and if desired washing with organic solvent and drying at suitable temperature.

The salt according to the present invention can be prepared by obtaining the dasatinib base as a solvate in solid state, and dissolving this solid dasatinib solvate in an organic solvent, and reacting with the desired acid, separating the crystallized salt and if desired washing with organic solvent and drying at suitable temperature.

The salts according to the present invention can also be prepared by drying the appropriate salt at suitable conditions whilst there is a solid phase morphologic conversion to another crystalline form.

The hydrous form of the salts according to the present invention can also be prepared by drying the appropriate salt at suitable conditions and storing in air in order to allow water absorption until stoichiometric quantity.

The hydrous form of the salts according to the present invention can also be prepared by performing the salt formation in the mixture of water and water-miscible solvent and the hydrous form of the precipitated crystalline salt is isolated.

The salt can be separated by known methods of pharmaceutical industry suitable for the separation of a solid phase and a liquid, such as filtration which is optionally carried out under atmospheric pressure or in vacuo or under pressure or by using a centrifuge.

For the salt formation according to the present invention organic or inorganic acids can be used, such as hydrogen bromide, cyclamic acid, methane sulfonic acid or p-toluenesulfonic acid.

The process can be carried out in an organic solvent, e.g. $C_{1-6}$ aliphatic alcohols, $C_{1-5}$ linear or ring ethers, $C_{1-6}$ esters, linear or branch chained symmetric or asymmetric ketons, dipolar-aprotic solvent or mixtures thereof or aqueous mixtures thereof.

It is preferred to use as organic solvent a $C_{1-4}$ ether, ester, alcohol, linear keton or a dipolar-aprotic solvent, particularly tetrahydrofurane, diethyl ether, ethyl acetate, acetonitrile, acetone, methanol, ethanol, 2-propanol, methyl-ethyl-ketone or mixtures or aqueous mixtures thereof.

Dasatinib (1) has more than one basic centre therefore the salts of the present invention may be prepared with different stoichiometry. Throughout the description 'mono' salt refers to a ratio of 1:1 of dasatinib and the corresponding salt; 'di' salt refers to a ratio of 1:2 of dasatinib and the corresponding salt.

The salt forming acid is preferably applied in a 0.3-3.0, preferably 0.5-2.5 molar equivalent amount related to the amount of the dasatinib. One may proceed preferably by using the solution of the organic acid and carrying out the reaction at a temperature between 0° C. and the boiling point of the solvent or at the boiling point of the solvent.

One may particularly preferably proceed by reacting the alcoholic solution or suspension of dasatinib with a solution containing a 0.3-3.0 molar equivalent of the acid at a temperature near to the boiling point of the solvent. The precipitated product is separated preferably by filtration.

One may also proceed by using the acid in solid crystalline form and performing the reaction at a temperature between 0° C. and the boiling point of the mixture or at the boiling point of the solvent.

One may particularly preferably proceed by reacting the alcoholic solution or suspension of dasatinib with 0.3-3.0 molar equivalent of the acid in solid crystalline form at a temperature near to the boiling point of the solvent. The precipitated product is separated preferably by filtration.

The new dasatinib salts of the present invention can be prepared by dissolving or suspending dasatinib base in a suitable solvent, preferably a C1-6 linear or branched chained alcohol, particularly ethanol, methanol or 2-propanol at a temperature between 0° C. and the reflux temperature of the solvent and adding a 0.3-3.0, preferably a 0.5-2.5 molar equivalent amount of an acid in solid form or as a solution. If the salt precipitates at the temperature of the addition or under cooling it is filtered, washed and dried. If the precipitation does not spontaneously take place seed crystals are added and the precipitated crystals are filtered. One may particularly preferably proceed by removing the solvent in vacuo and crystallizing the residue by adding a suitable solvent or solvent mixture, and finally filtering, washing and drying.

The new dasatinib salts of the present invention can be prepared by dissolving or suspending dasatinib base in a suitable solvent, preferably a C1-6 linear or branched chained alcohol, linear symmetric or asymmetric keton, particularly preferably ethanol, methanol, 2-propanol or acetone or aqueous mixtures thereof at a temperature between 0° C. and the reflux temperature of the solvent, preferably at room temperature and adding a 0.3-3.0, preferably a 0.5-2.5 molar equivalent amount of an acid in solid form or as a solution. If the salt precipitates it is filtered, washed and dried.

Dasatinib cyclamic acid (1:1) salt Form I is preferably prepared by stirring dasatinib free base with a linear alcohol-type solvent, preferably methanol and adding cyclamic acid in solid form at a temperature between 0° C. and the boiling point of the solvent, preferably at a temperature between room temperature and 80° C., more preferably at 70° C. Then after cooling the solvent is removed in vacuo and the residue is crystallized preferably by adding ethanol. The precipitated crystals are filtered, optionally washed and dried Dasatinib cyclamic acid (1:1) salt Form II is preferably prepared by stirring dasatinib free base or cyclamic acid with aqueous linear chained aliphatic keton-type solvent, preferably in aqueous acetone for four days, preferably at room temperature. If desired, the reaction mixture is cooled to 5-25° C., the precipitated crystals are filtered, optionally washed and dried.

Dasatinib hydrogen bromide (1:2) salt is preferably prepared by stirring dasatinib free base with an alcohol-type solvent, preferably ethanol and adding hydrogen bromide 47% aqueous solution at a temperature between 0° C. and the boiling point of the solvent, preferably at a temperature between room temperature and 80° C., more preferably at 70° C. Then after cooling the reaction mixture is stirred for four hours at room temperature. The precipitated crystals are filtered, optionally washed and dried.

Dasatinib methane sulfonic acid (1:2) salt is preferably prepared by stirring dasatinib free base with a linear chained aliphatic keton-type solvent, preferably ethyl-methyl-ketone and adding methane sulfonic acid at a temperature between 0° C. and the boiling point of the solvent, preferably at a temperature between room temperature and 80° C., more preferably at 60° C. and stirring the reaction mixture preferably at room temperature for 24 hours. The precipitated crystals are filtered, optionally washed and dried.

Dasatinib p-toluenesulfonic acid (1:1) dihydrate salt is preferably prepared by stirring dasatinib free base in an aqueous linear chained alcohol-type solvent, preferably in aqueous methanol and adding p-toluenesulfonic acid in solid form at a temperature between 0° C. and the boiling point of the solvent, preferably at room temperature and stirring the reaction mixture preferably at room temperature for 24 hours. If desired, the reaction mixture is cooled to 5-25° C., the precipitated crystals are filtered and dried.

Anhydrous dasatinib p-toluenesulfonic acid (1:1) salt Form I is preferably prepared by stirring dasatinib free base in a branched chained alcohol-type solvent, preferably in 2-propanol and adding p-toluenesulfonic acid monohydrate in solid form at a temperature between 0° C. and the boiling point of the solvent, preferably at a temperature between room temperature and 80° C., more preferably at 70 C and stirring the reaction mixture preferably at room temperature for 72 hours. The precipitated crystals are filtered, optionally washed and dried.

Anhydrous dasatinib p-toluenesulfonic acid (1:1) salt Form II is preferably prepared by drying p-toluenesulfonic acid (1:1) dihydrate salt under vacuo at a temperature between 40° C. and 60° C. preferably at 50° C., under a pressure of 5-10 mbar, preferably at a pressure of 8 mbar for 16 hours.

Dasatinib p-toluenesulfonic acid (1:1) salt methanol solvate is preferably prepared by stirring dasatinib free base in an aqueous linear chained alcohol-type solvent, preferably in methanol and adding p-toluenesulfonic acid monohydrate in solid form at a temperature between 0° C. and the boiling point of the solvent, preferably at a temperature between room temperature and 80° C., more preferably at 70° C. and stirring the reaction mixture preferably at room temperature for 20 hours. The precipitated crystals are filtered.

In course of the thermal stress test and the forced stability test the decompositions in a pharmaceutical composition occurring during storage are constructed essentially in an accelerated manner. The results of these tests predict that under forced storage conditions the new dasatinib salts of the present invention would be more stable than the salts known from the prior art. The advantageous properties of the new dasatinib salts of the present invention are significant from the point of view of the formulation of pharmaceutical compositions, the storage and the minimization of the harmful effects exerted in the human body.

As it is disclosed in WO2007/035874 paragraph [0096] dasatinib mono HCl includes a cavity or channel, which may be partially or fully occupied by solvent or a mixture of solvent. Our results also confirmed that the water adsorption property of this dasatinib mono HCl salt is changeable, especially after drying. The dasatinib diHCl salt disclosed in the same application also tends to adsorb water according to our DVS (dynamic vapor sorption) analysis, thus it is not regarded as a stable form. Further salts disclosed in the prior art also contain solvent adsorbed on the surface or in the form of solvate. These forms are nor suitable for pharmaceutical application. According to our experiments the most stable and suitable form disclosed in the prior art is the dasatinib base monohydrate. Therefore we carried out our comparative experiments between dasatinib base monohydrate and the new salts of the present invention.

The stability of the new dasatinib salts of the present invention were subjected to detailed tests. It has been surprisingly found that some of the dasatinib salts of the present invention show higher stability than the dasatinib forms known from the prior art in the storage tests carried out under various conditions. It has been found that the new salts of the present invention dasatinib cyclamic acid (1:1) salt Form I, dasatinib cyclamic acid (1:1) salt Form II, and anhydrous dasatinib p-toluenesulfonic acid (1:1) salt Form I proved to be particularly stable.

Our results regarding the quantity of the impurities and change thereof are shown in the tables below (expressed in percentage).

| Dasatinib monohydrate | | | | | | |
|---|---|---|---|---|---|---|
| | | | 3 week | | 6 week | |
| Impurity | RT | starting sample | 25° C./ 90% RH | 40° C./ 70% RH | 25° C./ 90% RH | 40° C./ 70% RH |
| Dasatinib imp 2 | 5.2 | 0.11 | 0.11 | 0.10 | 0.10 | 0.11 |
| Ethylenediamine intermedier | 9.3 | 0.03 | 0.06 | 0.08 | 0.03 | 0.03 |
| Deshydroxyethyl dasatinib | 11.0 | 0.12 | 0.12 | 0.12 | 0.12 | 0.12 |
| Dasatinib N-oxyde | 12.2 | 0.02 | 0.03 | 0.03 | <RL | 0.02 |

| Dasatinib monohydrate | | | | | | |
|---|---|---|---|---|---|---|
| | | | 3 week | | 6 week | |
| Impurity | RT | starting sample | 25° C./ 90% RH | 40° C./ 70% RH | 25° C./ 90% RH | 40° C./ 70% RH |
| Dasatinib imp 3 | 18.9 | 0.04 | 0.04 | 0.03 | 0.04 | 0.04 |
| | 19.6 | <RL | <RL | <RL | 0.02 | 0.02 |
| | 20.3 | 0.08 | 0.07 | 0.07 | 0.08 | 0.07 |
| Summary (%) | | 0.38 | 0.43 | 0.43 | 0.39 | 0.41 |

| Dasatinib cyclamic acid (1:1) salt Form I | | | | | | |
|---|---|---|---|---|---|---|
| | | | 3 week | | 6 week | |
| Impurity | RT | starting sample | 25° C./ 90% RH | 40° C./ 70% RH | 25° C./ 90% RH | 40° C./ 70% RH |
| Ethylenediamine intermedier | 9.0 | <RL | 0.02 | <RL | <RL | <RL |
| Deshydroxyethyl dasatinib | 11.0 | 0.03 | 0.03 | 0.03 | 0.03 | 0.03 |
| Dasatinib N-oxyde | 12.4 | 0.03 | 0.03 | 0.03 | 0.03 | 0.03 |
| | 15.5 | 0.03 | 0.03 | 0.03 | <RL | <RL |
| Summary (%) | | 0.09 | 0.11 | 0.09 | 0.06 | 0.06 |

| Anhydrous dasatinib p-toluenesulfonic acid (1:1) salt Form I | | | | | | |
|---|---|---|---|---|---|---|
| | | | 3 week | | 6 week | |
| Impurity | RT | starting sample | 25° C./ 90% RH | 40° C./ 70% RH | 25° C./ 90% RH | 40° C./ 70% RH |
| Ethylenediamine intermedier | 9.2 | <RL | <RL | 0.03 | <RL | <RL |
| | 15.5 | 0.03 | 0.03 | <RL | <RL | <RL |
| Summary (%) | | 0.03 | 0.03 | 0.03 | <RL | <RL |

| Dasatinib cyclamic acid (1:1) salt Form II | | | | | | |
|---|---|---|---|---|---|---|
| | | | 3 week | | 6 week | |
| Impurity | RT | starting sample | 25° C./ 90% RH | 40° C./ 70% RH | 25° C./ 90% RH | 40° C./ 70% RH |
| Ethylenediamine intermedier | 9.0 | 0.03 | 0.03 | 0.03 | 0.03 | 0.02 |
| Deshydroxyethyl dasatinib | 11.0 | 0.04 | 0.04 | 0.04 | 0.04 | 0.04 |
| Dasatinib N-oxyde | 12.4 | <RL | 0.04 | <RL | <RL | 0.03 |
| Summary (%) | | 0.07 | 0.11 | 0.07 | 0.07 | 0.09 |

Measuring conditions are the same as the determination of purity profile below.

The salts according to the present invention are particularly useful in the preparation of pharmaceutical compositions.

When orally administered the active ingredient shall be biologically available in a suitable narrow interval, and this bioavailability is dependent from several conditions, such as the solubility, stability and absorption of the pharmaceutical product in the gastrointestinal tract.

The aqueous solubility of dasatinib monohydrate is dependent on the pH of the aqueous medium. The normal pH in the stomach content is 1.2 to 1.8 Remington: *The Science and Practice of Pharmacy*, Volume 20 (2000, editor: A. R. Gennaro); Chapter 32; C. J. Perigard: *Clinical Analysis*]. In order to reduce side effects other pharmaceuticals are administered to patients with cancer, such as antacids and proton pump inhibitors. These can increase the gastric pH.

Considering the above mentioned facts our solubility measurements were carried out on three different pH values (pH 1, pH 4.5 and pH 6.8).

The salts of the present invention are suitable for preparation of pharmaceutical formulation, in which the variation in bioavailability is decreased compared to dasatinib base. Thus the pharmaceutical formulation containing the novel salts of the present invention provide better bioavailability than the Sprycel® contacting dasatinib monohydrate.

Determination of the Solubility of Dasatinib Salts (Measurement Conditions)

Preparation of Sample Mixture:

100 mg of dasatinib salt are weighed in a 20 ml Erlenmeyer flask whereupon 10 ml of medium are added and it is shaked for 6 hours at a temperature of 37° C. on 100 rpm. After sedimentation for 18 hours at a temperature of 37° C. the settled solution is filtered through a sieve with 0.45 μm pores and the solution is diluted up to 20 ml with medium.

| pH = 1 | | | | |
|---|---|---|---|---|
| Name: | Dasatinib solubility test | | | |
| Type of HPLC | Alliance e2695 | | | |
| Type of Column: | Inertsil ODS-4 5μ 4.0 × 150 mm 2HF41316 | | | |
| Medium | 0.1M HCl | | | |
| Port A | 0.1M ammonium acetate buffer (pH = 5.4) | | | |
| Port B | MeOH | | | |
| | Time (min) | flow rate (ml/min) | "A" | "B" |
| Gradient | 0 | 1 | 55 | 45 |
| | 2 | 1 | 55 | 45 |
| | 20 | 1 | 30 | 70 |
| | 25 | 1 | 30 | 70 |
| | 26 | 1 | 55 | 45 |
| | 30 | 1 | 55 | 45 |
| Flow rate: | 1 ml/min | | | |
| Pressure: | ~150-170 bar | | | |
| Temperature (HPLC) | Column: 25° C. | | Sample: 25° C. | |
| Wave: | 300 nm | | | |
| Volume of injection: | 20 μl | | | |
| Type of solubility instrument | GFL 1092 | | | |
| Temperature (of instrument) | 37° C. | | | |
| Shaking time | 6 hour | | | |
| Sedimentation time | 18 hour | | | |

| pH = 4.5 | | | | |
|---|---|---|---|---|
| Name: | Dasatinib solubility test | | | |
| Type of HPLC | Alliance e2695 | | | |
| Type of Column: | Inertsil ODS-4 5μ 4.0 × 150 mm 2HF41316 | | | |
| Medium | pH = 4.5 phosphate buffer | | | |
| Port A | 0.1M ammonium acetate buffer (pH = 5.4) | | | |
| Port B | MeOH | | | |
| | Time (min) | flow rate (ml/min) | "A" | "B" |
| Gradient | 0 | 1 | 55 | 45 |
| | 2 | 1 | 55 | 45 |
| | 20 | 1 | 30 | 70 |
| | 25 | 1 | 30 | 70 |
| | 26 | 1 | 55 | 45 |
| | 30 | 1 | 55 | 45 |
| Flow rate: | 1 ml/min | | | |
| Pressure: | ~150-170 bar | | | |
| Temperature (HPLC) | Column: 25° C. | | Sample: 25° C. | |
| Wave: | 300 nm | | | |
| Volume of injection: | 20 μl | | | |
| Type of solubility instrument | GFL 1092 | | | |
| Temperature (of instrument) | 37° C. | | | |
| Shaking time | 6 hour | | | |
| Sedimentation time | 18 hour | | | |

| pH = 6.8 | | | | |
|---|---|---|---|---|
| Name: | Dasatinib solubility test | | | |
| Type of HPLC | Alliance e2695 | | | |
| Type of Column: | Inertsil ODS-4 5μ 4.0 × 150 mm 2HF41316 | | | |
| Medium | pH = 6.8 phosphate buffer | | | |
| Port A | 0.1M ammonium acetate buffer (pH = 5.4) | | | |
| Port B | MeOH | | | |
| | Time (min) | flow rate (ml/min) | "A" | "B" |
| Gradient | 0 | 1 | 55 | 45 |
| | 2 | 1 | 55 | 45 |
| | 20 | 1 | 30 | 70 |
| | 25 | 1 | 30 | 70 |
| | 26 | 1 | 55 | 45 |
| | 30 | 1 | 55 | 45 |
| Flow rate: | 1 ml/min | | | |
| Pressure: | ~150-170 bar | | | |
| Temperature (HPLC) | Column: 25° C. | | Sample: 25° C. | |
| Wave: | 300 nm | | | |
| Volume of injection: | 20 μl | | | |
| Type instrument | GFL 1092 | | | |
| Temperature (of instrument) | 37° C. | | | |
| Shaking time | 6 hour | | | |
| Sedimentation time | 18 hour | | | |

Result of Measurements

| | Dasatinib monohydrate | dasatinib cyclamic acid (1:1) salt Form I | dasatinib cyclamic acid (1:1) salt Form II | dasatinib hydrogen bromide (1:2) salt |
|---|---|---|---|---|
| | | solubility (mg/ml) | | |
| 0.1M HCl | 5.757 | 8.533 | 8.862 | 7.994 |
| pH = 4.5 phosphate buffer | 0.555 | 6.194 | 4.544 | 1.056 |

|  | dasatinib mesilate (1:2) | dasatinib tosilate (1:1) dihydrate | dasatinib tosilate (1:1) Form I anhydrate | dasatinib tosilate (1:1) Form II anhydrate |
|---|---|---|---|---|
| pH = 6.8 phosphate buffer | 0.156 | 0.005 | 0.009 | 0.017 |

|  | dasatinib mesilate (1:2) | dasatinib tosilate (1:1) dihydrate | dasatinib tosilate (1:1) Form I anhydrate | dasatinib tosilate (1:1) Form II anhydrate |
|---|---|---|---|---|
|  |  | solubility (mg/ml) |  |  |
| 0.1M HCl | 7.333 | 4.898 | 5.365 | 5.702 |
| pH = 4.5 phosphate buffer | 0.805 | 1.641 | 4.510 | 2.805 |
| pH = 6.8 phosphate buffer | 0.017 | 0.010 | 0.009 | 0.011 |

It can be seen that the new dasatinib salts of the present invention at the most relevant pH 1 and pH 4.5 values show a significantly better solubility than the dasatinib monohydrate known from the prior art.

Determination of the Impurities of Dasatinib Salts by HPLC (Measurement Conditions)

| Type of HPLC: | Alliance e2695 |
|---|---|
| Type of column | Inertsil ODS-4 5μ 4.0 × 150 mm 2HF41316 |
| Eluent | MeOH:ammonium acetate buffer (pH = 4.5) = 75:25 |
| Port A | 0.1M ammonium acetate buffer (pH = 5.4) |
| Port B | MeOH |

|  | Time (min) | flow rate (ml/min) | "A" | "B" |
|---|---|---|---|---|
| Gradient | 0 | 1 | 55 | 45 |
|  | 2 | 1 | 55 | 45 |
|  | 20 | 1 | 30 | 70 |
|  | 25 | 1 | 30 | 70 |
|  | 26 | 1 | 55 | 45 |
|  | 30 | 1 | 55 | 45 |

| Flow rate: | 1 ml/min |  |
|---|---|---|
| Pressure: | ~150-170 bar |  |
| Temperature: | Column: 25° C. | Sample: 25° C. |
| Wave: | 248 nm, 300 nm |  |
| Volume of injection: | 20 μl |  |

Impurity Data Measured by HPLC of the Salt:

|  | Dasatinib monohydrate | dasatinib cyclamic acid (1:1) salt Form I | dasatinib cyclamic acid (1:1) salt Form II | dasatinib hydrogen bromide (1:2) salt |
|---|---|---|---|---|
|  |  | detected impurity (%) |  |  |
| Dasatinib impurity 2 | 0.08 | — | — | — |
| Ethylene-diamin intermedier | 0.04 | 0.06 | 0.03 | 0.04 |
| Deshydroxy-ethyl dasatinib | 0.12 | 0.04 | 0.03 | 0.18 |
| Dasatinib N-oxyde | 0.20 | 0.03 | — | — |
| Dasatinib impurity 3 | 0.04 | — | — | — |
| Unknown (sum) | 0.09 | 0.06 | — | 0.05 |
| Sum | 0.57 | 0.19 | 0.06 | 0.27 |

|  | dasatinib mesilate (1:2) | dasatinib tosilate (1:1) dihydrate | dasatinib tosilate (1:1) Form I anhydrate | dasatinib tosilate (1:1) Form II anhydrate |
|---|---|---|---|---|
|  |  | detected impurity (%) |  |  |
| Dasatinib impurity 2 | — | — | — | — |
| Ethylene-diamin intermedier | 0.09 | — | 0.04 | — |
| Deshydroxy-ethyl dasatinib | 0.05 | 0.04 | 0.04 | 0.03 |
| Dasatinib N-oxyde | 0.03 | 0.02 | — | — |
| Dasatinib impurity 3 | — | — | — | — |
| Unknown (sum) | 0.06 | — | 0.02 | — |
| Sum | 0.23 | 0.06 | 0.10 | 0.03 |

The new dasatinib salts of the present invention can be prepared in higher purity than the dasatinib monohydrate known from the prior art. Dasatinib cyclamic acid (1:1) salt Form II, dasatinib p-toluenesulfonic acid (1:1) dihydrate salt, anhydrous dasatinib p-toluenesulfonic acid (1:1) salt Form I and Form II can be obtained in a particularly pure form.

Thus in conclusion it has been surprisingly found that the new salts, especially the dasatinib cyclamate salt of the present invention provide for a better solubility profile at the most relevant acidic range and at the same time also show better stability during storage and can be prepared in higher purity than the prior art forms of dasatinib.

According to a further aspect of the present invention there are provided pharmaceutical compositions comprising a therapeutically effective amount of a dasatinib salt of the present invention and if desired one or more pharmaceutically active carrier. According to a further aspect of the present invention there is provided a process for the preparation of the above pharmaceutical compositions which comprises admixing an dasatinib salt or a mixture thereof with pharmaceutically acceptable solid or liquid diluents and/or auxiliary agents and bringing the mixture to a galenic composition.

The pharmaceutical compositions of the invention can be administered preferably orally. Such oral compositions may be e.g. tablets, capsules, dragées, solutions, elixirs, suspensions or emulsions.

The pharmaceutical compositions according to the present invention may contain conventional pharmaceutical carriers and/or auxiliary agents. As carrier e.g. magnesium carbonate, magnesium stearate, talc, sugar, lactose, pectin, dextrin, starch, gelatin, tragacanth, methyl cellulose, sodium carboxymethyl cellulose, low melting wax, PEG, cocoa butter etc. can be used. In case of capsules the carrier often serves as the capsule wall material so that no additional carrier is required. Chartula and lozenge are further oral pharmaceutical compositions. Particularly preferred oral administration forms are the powders, pirules, chartula and lozenges.

The tablets are prepared by admixing the active ingredient with suitable carriers in an appropriate ratio and from this mixture tablets of desired shape and size are pressed.

The powders are prepared by admixing the finely powdered active ingredient with the carriers. The liquid compositions may be solutions, suspensions and emulsions which can also be sustained release compositions. Aqueous solutions and aqueous propylene glycol solutions proved to be advantageous. Compositions suitable for parenteral administration can be prepared preferably in the form of aqueous polyethylene glycol solutions.

The pharmaceutical compositions of the invention can be preferably prepared in the form of dosage units which contain the desired amount of the active ingredient. The dosage units can be put on the market in the form of packages comprising separated amounts of the compositions e.g. packed tablets, capsules, vials or ampoules which contain the powder. The term "dosage unit" relates to the capsules, chartula, lozenge and also to the package comprising a suitable amount of dosage units.

The pharmaceutical compositions of the present invention can be prepared by conventional methods of pharmaceutical industry. The pharmaceutical compositions of the present invention may contain further pharmaceutical active ingredients which are compatible with the new salts of dasatinib or mixtures thereof.

Further object of the present invention relates to dasatinib salts of the present invention for use in medicine. Further object of the present invention relates to dasatinib salts of the present invention for the preparation of pharmaceutical compositions for the treatment of cancer. Furthermore the present invention relates to dasatinib salts of the present invention for use in the treatment of cancer. Our invention further relates to a method of treating cancer in a patient comprising administering to said patient an amount of a dasatinib salt of the present invention. Cancer is preferably chronic myeloid leukaemia (CML), more preferably Philadelphia chromosome positive (Ph+) acute lymphoblastic leukemia (ALL) and lymphoid blast CML with resistance or intolerance to prior therapy The advantage of the present invention is that the compounds of the present invention are substances of uniform morphology and have an advantageous crystal form. For this reason the salts of the present invention possess preferable and reproducible properties, such as dissolving velocity, bioavailability, chemical stability and processing characteristics e.g. filtration, drying and tabletting properties.

The active ingredients of the present invention can be prepared by procedures readily suitable for industrial scale manufacture.

The present invention is elucidated by the following examples without limiting the scope of the invention to the examples.

EXAMPLES

The dasatinib base used in the following Examples can be prepared for example according to WO2005/077945.

NMR Measurement Condition:

The NMR spectra of the new salts according to the present invention is registered by use of the following apparatus: VARIAN INOVA 500/500 MHz/, BRUKER AVANCE III 400/400 MHz/. NMR measurements of the new salts were carried out in solution-phase, deuterated dimethyl sulfoxide (DMSO-$d_6$) were used as solvent.

X-Ray Powder Diffraction Measurements:

The X-ray powder diffraction data of dasatinib cyclamic acid (1:1) salt Form I, dasatinib cyclamic acid (1:1) salt Form II, dasatinib hydrogen bromide (1:2) salt, dasatinib methane sulfonic acid (1:2) salt, dasatinib p-toluenesulfonic acid (1:1) dihydrate salt, anhydrous dasatinib p-toluenesulfonic acid (1:1) salt Form I, anhydrous dasatinib p-toluenesulfonic acid (1:1) salt Form II, dasatinib p-toluenesulfonic acid (1:1) salt methanol solvate were obtained under the following measuring conditions:

Apparatus: Bruker D8 Advance X-ray powder diffractometer

Radiation: CuK$\alpha_1$ ($\lambda$=1.54060 Å), CuK$\alpha_2$ ($\lambda$=1.54439 Å)

Accelerating voltage: 40 kV

Anode current: 40 mA

Arrangement: Göbel-mirror (parallel radiation), 9-position sample changer, transmissive arrangement Detector: Bruker LynxEye Soller: 2.5°

Orifices: source side: 0.6 mm divergence slit
detector side: 8 mm slit

Measuring range: continuous θ/2θ scan, 4-35 °2θ

Time for one step: 1.2 sec

Step interval: 0.02 °2θ

Sample preparation: not powdered sample between Mylar foils, room temperature

Rotation speed of the sample holder: 0.5 rotation/sec

Measurement cycles: 1

Measurement time: 35 minutes

Example 1

Preparation of Dasatinib Cyclamic Acid (1:1) Salt Form I

Into an apparatus 1.000 g (2.05 mmol) of dasatinib base and 70 cm$^3$ of methanol are weighted under rigorous stirring and the mixture is heated up to the temperature of 70° C. To the solution 0.367 g (2.05 mmol) cyclamic acid in solid form are added under stirring at this temperature and the solution is cooled to room temperature after total dissolution of the acid and it is evaporated. To the oily residue 10 cm$^3$ of methanol are added and the crystallization is initiated by scratching. The precipitated crystals are filtered and washed with a little amount of cold ethanol and tert-butyl-methyl-ether and dried under vacuo for 24 hours at a temperature of 40° C., on 5.2 mbar.

Yield: 1.129 g (93.4%)

Mp.: no characteristic value, thermal decomposition observed above 200° C.

Analysis for the Formula $C_{22}H_{26}ClN_7O_2S \cdot C_6H_{13}NO_3S$ (667.25):

| Calc. | C: 50.40% | H: 5.89% | N: 16.79% | Cl: 5.31% | S: 9.61% |
| Found | C: 50.48% | H: 5.99% | N: 16.92% | Cl: 5.26% | S: 9.86% |

IR (KBr, cm$^{-1}$): 3310, 3166, 2931, 2854, 1632, 1609, 1582, 1502, 1451, 1411, 1312, 1279, 1222, 1193, 1139, 1068, 1024, 996, 816, 771.

$^1$H-NMR (DMSO-$d_6$, 400 MHz): 10.55 (b, 1H), 9.88 (b, 1H), 8.23 (s, 1H), 7.40 (m, 1H), 7.29 (m, 1H), 7.26 (m, 1H), 6.14 (s, 1H), 5.03 (b, 1H), 3.70 (m, 6H), 3.02 (m, 1H), 3.00 (m, 1H), 2.93 (m, 2H), 2.43 (s, 3H), 2.24 (s, 3H), 1.99 (m, 2H), 1.65 (m, 2H), 1.51 (m, 1H), 1.13 (m, 5H).

$^{13}$C-NMR (DMSO-$d_6$, 125 MHz): 165.48, 162.30, 160.05, 157.29, 140.96, 138.97, 133.66, 132.60, 129.18, 128.33, 127.16, 126.01, 83.29, 58.76, 56.38, 53.28, 51.59, 41.90, 32.41, 25.70, 25.44, 24.65, 18.44.

Example 2

Preparation of Dasatinib Cyclamic Acid (1:1) Salt Form II

Into an apparatus 1.000 g (2.05 mmol) dasatinib base and 0.367 g (2.05 mmol) cyclamic acid and 20 cm$^3$ of aqueous aceton (ratio of water acetone is 10:1) weighted under stirring for 4 days at room temperature. The precipitated crystals are filtered and washed with a little amount of cold ethanol and tert-butyl-methyl-ether and dried under vacuo for 24 hours, at a temperature of 45° C., on 11 mbar.

Yield: 1.353 g (96.7%)

Mp.: no characteristic value, thermal decomposition observed above 200° C.

Analysis for the Formula $C_{22}H_{26}ClN_7O_2S.C_6H_{13}NO_3S$ (667.25):

| | | | | | |
|---|---|---|---|---|---|
| Calc | C: 50.40% | H: 5.89% | N: 16.79% | Cl: 5.31% | S: 9.61% |
| Found | C: 50.65% | H: 5.97% | N: 16.93% | Cl: 5.45% | S: 9.51% |

IR (KBr, cm$^{-1}$): 3364, 3249, 3012, 2930, 2852, 1625, 1612, 1574, 1527, 1498, 1452, 1430, 1414, 1396, 1338, 1303, 1190, 1029, 983, 908, 794, 726, 613, 530.

Example 3

Preparation of Dasatinib Hydrogen Bromide (1:2) Salt

Into an apparatus 1.000 g (2.05 mmol) of dasatinib base and 20 cm$^3$ of ethanol are weighted under rigorous stirring and the mixture is heated up to the temperature of 70° C. To the reaction mixture 0.475 cm$^3$ (4.11 mmol) 47% aqueous hydrogen bromide solution are added under stirring at this temperature. Precipitation starts immediately after dissolution of the base. The mixture is cooled to room temperature by stopping heating under stirring and it is stirred for further 4 hour at room temperature. The precipitated crystals are filtered and washed with a little amount of cold ethanol and tert-butyl-methyl-ether and dried.

Yield: 1.301 g (97.7%)

Mp.: 305-312° C.

Analysis for the Formula $C_{22}H_{26}ClN_7O_2S.2\ HBr$ (649.85):

| | | | | | |
|---|---|---|---|---|---|
| Calc | C: 40.66% | H: 4.34% | N: 15.09% | Br: 24.59% | Cl: 5.46% S: 4.93% |
| Found | C: 40.51% | H: 4.27% | N: 14.96% | Br: 24.47% | Cl: 5.51% S: 4.86% |

IR (KBr, cm$^{-1}$): 3215, 2863, 1648, 1593, 1546, 1501, 1467, 1285, 1241, 1153, 1063, 1037, 991, 904, 860, 809, 746, 625.

$^1$H-NMR (DMSO-d$_6$, 500 MHz): 11.63 (b, 1H), 9.92 (bs, 1H), 9.81 (b, 1H), 8.27 (s, 1H), 7.40 (m, 1H), 7.29 (m, 1H), 7.26 (m, 1H), 6.20 (s, 1H), 4.33 (b, 2H), 3.78 (m, 2H), 3.61 (m, 2H), 3.36 (m, 2H), 3.25 (m, 2H), 3.14 (m, 2H), 2.46 (s, 3H), 2.24 (s, 3H).

Example 4

Preparation of Dasatinib Methane Sulfonic Acid (1:2) Salt

Into an apparatus 1.000 g (2.05 mmol) of dasatinib base and 20 cm$^3$ of ethyl-methyl-ketone are weighted under stirring and the mixture is heated up to the temperature of 60° C. To the suspension 0.279 cm$^3$ (4.31 mmol; 2.1 ekv.) of methane sulfonic acid are added under stirring at this temperature. The suspension becomes aggregated. The mixture is cooled to room temperature by stopping heating. The solid aggregated can be powdered. The mixture is stirred for further 2 4 hour at room temperature. The precipitated crystals are filtered and washed with 3×10 cm$^3$ of tert-butyl-methyl-ether and dried under vacuo for 20 hours, at a temperature of 50° C., on 10 mbar.

Yield: 1.306 g (93.7%)

Mp.: 208-218° C.

Analysis for the Formula $C_{22}H_{26}ClN_7O_2S.2\ CH_4O_3S$ (680.22):

| | | | | | |
|---|---|---|---|---|---|
| Calc | C: 42.38% | H: 5.04% | N: 14.41% | Cl: 5.21% | S: 14.14% |
| Found | C: 42.09% | H: 5.13% | N: 14.26% | Cl: 5.10% | S: 13.99% |

IR (KBr, cm$^{-1}$): 3278, 3013, 1671, 1626, 1540, 1511, 1485, 1406, 1325, 1288, 1210, 1163, 1042, 986, 896, 865, 813, 771, 712, 627, 550, 524.

$^1$H-NMR (DMSO-d$_6$, 400 MHz): 11.68 (b, 1H), 9.92 (bs, 1H), 9.73 (b, 1H), 8.25 (s, 1H), 7.40 (m, 1H), 7.29 (m, 1H), 7.26 (m, 1H), 6.23 (s, 1H), 4.36 (m, 2H), 3.77 (m, 2H), 3.60 (m, 2H), 3.34 (m, 2H), 3.23 (m, 2H), 3.12 (m, 2H), 2.46 (s, 3H), 2.39 (s, 6H), 2.24 (s, 3H).

Example 5

Preparation of Dasatinib p-Toluenesulfonic Acid (1:1) Dihydrate Salt

Into an apparatus 2.00 g (4.1 mmol) of dasatinib base and the mixture of 30 cm$^3$ of methanol and 10 cm$^3$ water are weighted and the mixture is kept under stirring for two minutes. To the suspension 0.780 g (4.1 mmol) p-tulouenesulfonic acid monohydrate are added under stirring. The solution in not clear because the precipitation of the dihydrate salt is started. The reaction mixture became dense but it can be stirred further for 24 hour at room temperature on 1300 rpm. The precipitated crystals are filtered and dried.

Yield: 1.918 g (67.3%)

Mp.: 196-210° C.

Analysis for the Formula $C_{22}H_{26}ClN_7O_2S.C_7H_8O_3S.2\ H_2O$ (696.25):

| | | | | | |
|---|---|---|---|---|---|
| Calc | C: 50.02% | H: 5.50% | N: 14.08% | Cl: 5.09% | S: 9.21% |
| Found | C: 50.37% | H: 5.07% | N: 14.18% | Cl: 5.16% | S: 9.12% |

Water contain is 5.3% determined by Karl Fischer titration. This shows good correspondence with the calculated value of 5.18%.

IR (KBr, cm$^{-1}$): 3385, 3205, 3013, 1609, 1584, 1496, 1416, 1318, 1291, 1167, 1122, 1031, 1008, 818, 777, 683, 565.

$^1$H-NMR (DMSO-d$_6$, 400 MHz): 11.64 (bs, 1H). 9.92 (bs, 1H), 9.68 (b, 1H), 8.25 (s, 1H), 7.48 (d, J=8 Hz, 2H), 7.40 (m, 1H), 7.29 (m, 1H), 7.26 (m, 1H), 7.11 (d, J=7.9 Hz, 2H), 6.17 (s, 1H), 5.42 (b, 1H), 4.33 (m, 2H), 3.77 (m, 2H), 3.58 (m, 2H), 3.35 (m, 2H), 3.23 (m, 2H), 3.10 (m, 2H), 2.45 (s, 3H), 2.29 (s, 3H), 2.24 (s, 3H).

Example 6

Preparation of Anhydrous Dasatinib p-Toluenesulfonic Acid (1:1) Salt Form I

Into an apparatus 1.00 g (2.05 mmol) of dasatinib base and 20 cm$^3$ of 2-propanol are weighted and the mixture is heated up to the temperature of 70° C. under rigorous stirring. To the reaction mixture 0.390 g (2.05 mmol) p-tulouenesulfonic acid monohydrate are added under stirring at this temperature. The base starts to dissolve and precipitate appears then by stopping the heating the reaction mixture is stirred further for 72 hours under room temperature. The precipitated crystals are filtered and washed with a little amount of cold 2-propanol and tert-butyl-methyl-ether and dried.

Yield: 1.183 g (87.4%)

Mp.: 251-261° C.

Analysis for the Formula $C_{22}H_{26}ClN_7O_2S \cdot C_7H_8O_3S$ (660.22):

| Calc | C: 52.76% | H: 5.19% | N: 14.85% | Cl: 5.37% | S: 9.71% |
| Found | C: 52.80% | H: 5.26% | N: 14.77% | Cl: 5.44% | S: 9.63% |

$^1$H-NMR (DMSO-$d_6$, 400 MHz): see Example 5.

IR (KBr, cm$^{-1}$): 3322, 3170, 3019, 2924, 2750, 1635, 1610, 1585, 1501, 1454, 1412, 1291, 1279, 1225, 1192, 1154, 1118, 1066, 1029, 1005, 814, 769, 683, 588, 571.

Example 7

Preparation of Anhydrous Dasatinib p-Toluenesulfonic Acid (1:1) Salt Form II

The dasatinib p-toluenesulfonic acid (1:1) dihydrate salt prepared according the Example 5 is dried at a temperature of 50° C., on 8 mbar, for 16 hours. Thus anhydrous dasatinib p-toluenesulfonic acid (1:1) salt Form II is obtained.

IR (KBr, cm$^{-1}$): 3180, 3015, 2837, 1620, 1605, 1583, 1519, 1495, 1412, 1388, 1321, 1292, 1272, 1206, 1187, 1122, 1031, 1009, 963, 836, 675, 563.

Example 8

Preparation of Dasatinib p-Toluenesulfonic Acid (1:1) Salt Methanol Solvate.

Into an apparatus 1.00 g (2.05 mmol) of dasatinib base and 20 cm$^3$ of methanol are weighted and the mixture is heated up to the temperature of 70° C. under rigorous stirring. The mixture is stirred for 5 minutes at this temperature. To the reaction mixture 0.390 g (2.05 mmol) p-tulouenesulfonic acid monohydrate are added under stirring by stopping the heating. Precipitate appears while the mixture is stirred for 20 hours at room temperature. The precipitated crystals are filtered and dried slowly.

TG data shows 4.2 w/w % of mass loss up to the temperature of 120° C., which shows good correspondence to the value of 4.6 w/w % calculated on methanol solvate.

The invention claimed is:

1. A Dasatinib product, which is
Dasatinib cyclamic acid salt, which is in amorphous or crystalline form, and/or is a hydrate or solvate thereof;
Dasatinib hydrogen bromide (1:2) salt having the following characteristic X-ray powder diffraction peaks: 2θ (±0.2 °2θ): 19.75; 24.39; 29.82;
Dasatinib methane sulfonic acid (1:2) salt having the following characteristic X-ray powder diffraction peaks: 2θ (±0.2 °2θ): 4.26; 17.52; 22.66;
Dasatinib p-toluenesulfonic acid (1:1) dihydrate salt having the following characteristic X-ray powder diffraction peaks: 2θ (±0.2 °2θ): 6.41; 17.68; 19.41;
anhydrous Dasatinib p-toluenesulfonic acid (1:1) salt Form I having the following characteristic X-ray powder diffraction peaks: 2θ (±0.2 °2θ): 10.21; 12.77; 16.74;
anhydrous Dasatinib p-toluenesulfonic acid (1:1) salt Form II having the following characteristic X-ray powder diffraction peaks: 2θ (±0.2 °2θ): 12.17; 14.57; 24.42; or
Dasatinib p-toluenesulfonic acid (1:1) salt methanol solvate having the following characteristic X-ray powder diffraction peaks: 2θ (±0.2 °2θ): 18.36; 19.50; 22.52.

2. The Dasatinib product according to claim 1, which is Dasatinib cyclamic acid (1:1) salt Form I having the following characteristic X-ray powder diffraction peaks: 2θ (±0.2 °2θ): 10.11; 18.81; 19.83.

3. The Dasatinib product according to claim 1, which is Dasatinib cyclamic acid (1:1) salt Form II having the following characteristic X-ray powder diffraction peaks: 2θ (±0.2 °2θ): 4.24; 8.43; 14.80.

4. The Dasatinib product according to claim 1, which is Dasatinib hydrogen bromide (1:2) salt having the following characteristic X-ray powder diffraction peaks: 2θ (±0.2 °2θ): 19.75; 24.39; 29.82.

5. The Dasatinib product according to claim 1, which is Dasatinib methane sulfonic acid (1:2) salt having the following characteristic X-ray powder diffraction peaks: 2θ (±0.2 °2θ): 4.26; 17.52; 22.66.

6. The Dasatinib product according to claim 1, which is Dasatinib p-toluenesulfonic acid (1:1) dihydrate salt having the following characteristic X-ray powder diffraction peaks: 2θ (±0.2 °2θ): 6.41; 17.68; 19.41.

7. The Dasatinib product according to claim 1, which is anhydrous Dasatinib p-toluenesulfonic acid (1:1) salt Form I having the following characteristic X-ray powder diffraction peaks: 2θ (±0.2 °2θ): 10.21; 12.77; 16.74.

8. The Dasatinib product according to claim 1, which is anhydrous Dasatinib p-toluenesulfonic acid (1:1) salt Form II having the following characteristic X-ray powder diffraction peaks: 2θ (±0.2 °2θ): 12.17; 14.57; 24.42.

9. The Dasatinib product according to claim 1, which is Dasatinib p-toluenesulfonic acid (1:1) salt methanol solvate having the following characteristic X-ray powder diffraction peaks: 2θ (±0.2 °2θ): 18.36; 19.50; 22.52.

10. A process for preparing the Dasatinib product according to claim 1, comprising reacting Dasatinib base in an organic solvent or in a mixture of an organic solvent and water with an organic or inorganic acid and separating the Dasatinib salt formed.

11. The process according to claim 10, wherein the organic or inorganic acid is hydrogen-bromide, cyclamic acid, methansulfonic acid, or p-toluenesulfonic acid, and after separating the Dasatinib salt formed, optionally drying.

12. The process according to claim 11, wherein 0.3-3.0 molar equivalent amount of acid is reacted.

13. The process according to claim 11, wherein the organic solvent is selected from the group consisting of $C_{1-4}$ aliphatic alcohols, linear symmetric ketones, or asymmetric ketones, $C_{1-5}$ linear ethers, ring ethers, $C_{1-6}$ esters, and dipolar-aprotic solvents, or is a mixture thereof or an aqueous mixture thereof.

14. The process according to claim 13 wherein the organic solvent is tetrahydrofurane, diethyl ether, ethyl acetate, acetonitrile, acetone, methanol, ethanol, 2-propanol, or methyl-ethyl-ketone or a mixture thereof or an aqueous mixture thereof.

15. The process according to claim 10, wherein the reaction is carried out at a temperature between 0° C. and the boiling point of the solvent.

16. A pharmaceutical composition, comprising the Dasatinib product according to claim 1 in an admixture with one or more pharmaceutical auxiliary agents.

17. A method for preparing the pharmaceutical composition according to claim 16, comprising admixing a therapeutically effective amount of said Dasatinib product with a pharmaceutically acceptable carrier and optionally with further pharmaceutically acceptable auxiliary agents and bringing the mixture into a galenic form.

18. A method of treating cancer, including chronic myeloid leukemia in a patient comprising administering to said patient an effective amount of the Dasatinib product according to claim 1.

19. The Dasatinib product according to claim 1, which has the following characteristic X-ray powder diffraction pattern as depicted in:

FIG. 1 for the Dasatinib cyclamate (1:1) Form I;
FIG. 2 for the Dasatinib cyclamate (1:1) Form II;
FIG. 3 for the Dasatinib hydrogen bromide (1:2) salt;
FIG. 4 for the Dasatinib mesilate (1:2);
FIG. 5 for the Dasatinib tosilate (1:1) dihydrate;
FIG. 6 for the anhydrous Dasatinib tosilate (1:1) Form I;
FIG. 7 for the anhydrous Dasatinib tosilate (1:1) Form II; or
FIG. 8 for the Dasatinib tosilate (1:1) methanol solvate.

20. The Dasatinib product according to claim 1, which has the following characteristic X-ray powder diffraction peaks (±0.2 °2θ):

for the Dasatinib cyclamic acid (1:1) salt Form I: 7.64; 10.11; 13.74; 18.81; 19.83; 21.49; 21.78; 22.94; 24.79; 31.59;

for the Dasatinib cyclamate (1:1) Form II: 4.24; 8.43; 8.73; 12.34; 14.80; 17.25; 20.81; 21.12; 25.91; 26.54;

for the Dasatinib hydrogen bromide (1:2) salt: 10.98; 11.51; 12.32; 16.07; 19.75; 21.67; 24.39; 24.78; 29.82; 32.20;

for the Dasatinib mesilate (1:2): 4.26; 9.86; 10.16; 13.66; 17.52; 18.13; 20.33; 22.66; 28.45; 30.97;

for the Dasatinib tosilate (1:1) dihydrate: 6.41; 11.79; 13.05; 13.80; 17.68; 18.55; 19.41; 20.73; 22.51; 23.96;

for the anhydrous Dasatinib tosilate (1:1) Form I: 10.21; 11.09; 12.77; 13.75; 16.74; 17.76; 18.68; 19.95; 21.32; 29.04;

for the anhydrous Dasatinib tosilate (1:1) Form II: 6.37; 9.54; 11.90; 12.17; 14.22; 14.57; 18.39; 19.78; 24.42; 25.46; or for the Dasatinib tosilate (1:1) methanol solvate: 6.35; 9.25; 13.83; 18.36; 19.50; 21.48; 22.52; 24.02; 24.94; 27.16.

21. The Dasatinib product according to claim 1, which is Dasatinib cyclamic acid salt in crystalline form.

* * * * *